United States Patent
Kamiya

(10) Patent No.: US 9,265,467 B2
(45) Date of Patent: Feb. 23, 2016

(54) RADIATION IMAGING SYSTEM, METHOD FOR TAKING CONTINUOUS RADIOGRAPHIC IMAGE, AND RADIATION IMAGE DETECTING DEVICE

(75) Inventor: Takeshi Kamiya, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 363 days.

(21) Appl. No.: 13/593,570

(22) Filed: Aug. 24, 2012

(65) Prior Publication Data
US 2013/0077744 A1   Mar. 28, 2013

(30) Foreign Application Priority Data

Sep. 27, 2011  (JP) ................................ 2011-210146

(51) Int. Cl.
*A61B 6/10*   (2006.01)
*A61B 6/06*   (2006.01)
*A61B 6/00*   (2006.01)

(52) U.S. Cl.
CPC ................. *A61B 6/06* (2013.01); *A61B 6/4233* (2013.01); *A61B 6/5241* (2013.01); *A61B 6/542* (2013.01); *A61B 6/548* (2013.01); *A61B 6/544* (2013.01)

(58) Field of Classification Search
CPC .... A61B 6/4233; A61B 6/5241; A61B 6/542; A61B 6/544; A61B 6/547; A61B 6/06; A61B 6/548
USPC ................................................ 378/62, 97, 98
See application file for complete search history.

(56) References Cited

U.S. PATENT DOCUMENTS

| | | | | |
|---|---|---|---|---|
| 6,198,800 | B1 * | 3/2001 | Garland et al. | 378/98.7 |
| 6,304,625 | B1 * | 10/2001 | Senzig | 378/4 |
| 2004/0096035 | A1 * | 5/2004 | Yamazaki et al. | 378/97 |

(Continued)

FOREIGN PATENT DOCUMENTS

| | | |
|---|---|---|
| JP | 08-033621 | 2/1996 |
| JP | 2000-037372 | 2/2000 |

(Continued)

OTHER PUBLICATIONS

Extended European Search Report dated Oct. 30, 2012 issued by the European Patent Office in corresponding European Patent Application No. 12181875.1, 13 pages.

(Continued)

*Primary Examiner* — Robert Kim
*Assistant Examiner* — Wyatt Stoffa
(74) *Attorney, Agent, or Firm* — Young & Thompson

(57) ABSTRACT

In continuous radiography, while a patient stands in front of an imaging support, a total image capture field is determined. The total image capture field is divided into small image capture fields. A map scaling section scales up or down a full spine irradiation area map in accordance with the size of the total image capture field. A map dividing section divides the scaled map into small maps corresponding to the small image capture fields. In each division exposure, a detection pixel selector selects one or more detection pixels belonging to an irradiation area defined by the small map, out of all detection pixels distributed in an imaging surface of an electronic cassette. If an integration value of a detection signal from the selected detection pixel reaches a threshold value, X-ray emission is stopped. Division X-ray images obtained by the division exposures are merged into a single continuous X-ray image.

15 Claims, 18 Drawing Sheets

(56) References Cited

U.S. PATENT DOCUMENTS

| | | | |
|---|---|---|---|
| 2004/0161075 A1* | 8/2004 | Amitani | 378/37 |
| 2008/0152088 A1* | 6/2008 | Wang et al. | 378/98.12 |
| 2010/0290592 A1* | 11/2010 | Yamada | 378/114 |
| 2011/0038454 A1* | 2/2011 | Minnigh et al. | 378/62 |
| 2012/0224672 A1* | 9/2012 | Yamada | 378/98 |
| 2013/0202086 A1* | 8/2013 | Tsuji | 378/62 |
| 2013/0315372 A1* | 11/2013 | Behiels | 378/62 |
| 2014/0205066 A1* | 7/2014 | Kitagawa et al. | 378/62 |

FOREIGN PATENT DOCUMENTS

| | | |
|---|---|---|
| JP | 2000-100597 | 4/2000 |
| JP | 2002-000590 | 1/2002 |
| JP | 2004-251892 | 9/2004 |
| JP | 2009-240568 | 10/2009 |
| JP | 2010-246778 | 11/2010 |
| JP | 2011-139761 | 7/2011 |

OTHER PUBLICATIONS

EP Office Action dated Nov. 4, 2013, with English translation; Application No. 12 181 875.1.

Notification of Reasons for Refusal issued by the Japanese Patent Office on Aug. 14, 2013 in Japanese Patent Application No. 2011-210146, with English translation.

\* cited by examiner

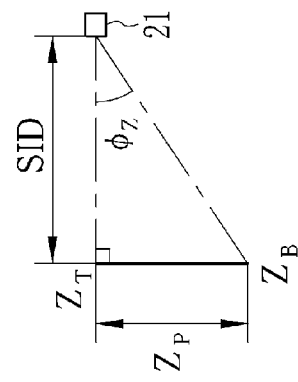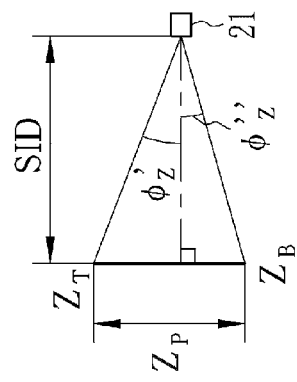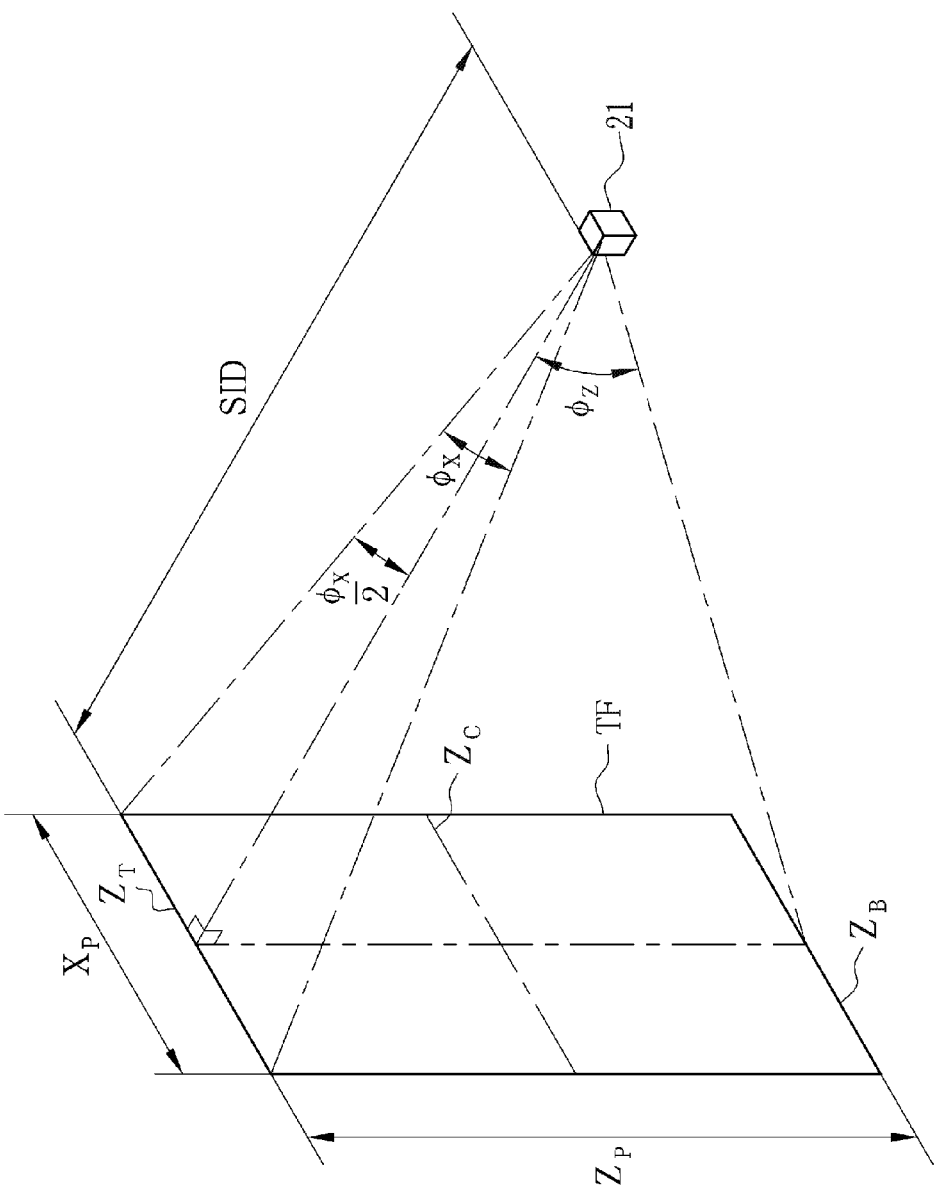

FIG. 9A

| IRRADIATION AREA | UPPER LEFT POINT | LOWER RIGHT POINT |
|---|---|---|
| SPINE | $X_1, 0$ | $X_3, Z_1$ |
| PELVIS | $X_2, Z_1$ | $X_4, Z_2$ |

FIG. 9B

| IRRADIATION AREA | UPPER LEFT POINT | LOWER RIGHT POINT |
|---|---|---|
| PELVIS | $X_2, 0$ | $X_4, Z_3$ |
| RIGHT KNEE | $X_5, Z_4$ | $X_6, Z_5$ |
| LEFT KNEE | $X_7, Z_4$ | $X_8, Z_5$ |
| RIGHT ANKLE | $X_9, Z_6$ | $X_{10}, Z_7$ |
| LEFT ANKLE | $X_{11}, Z_6$ | $X_{12}, Z_7$ |

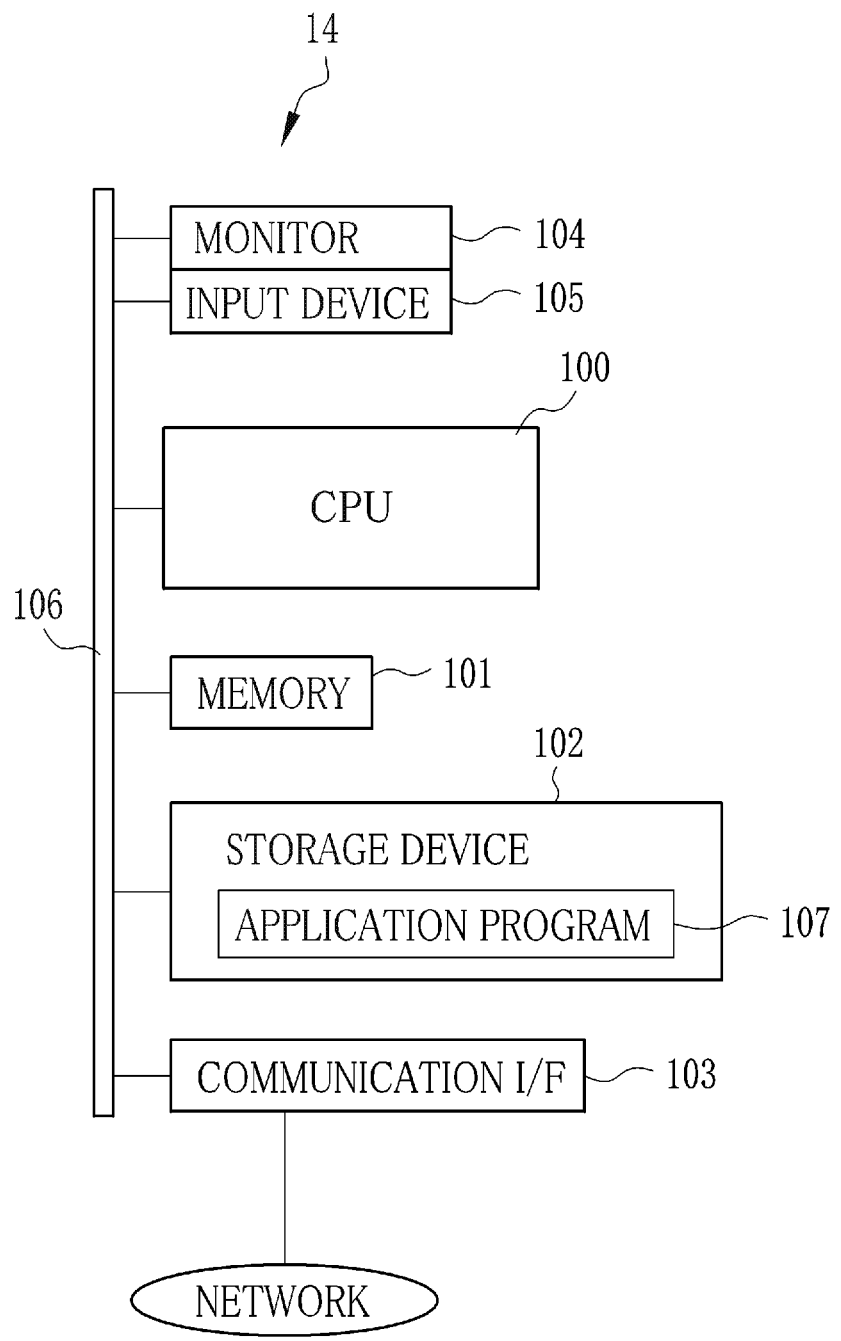

FIG. 13
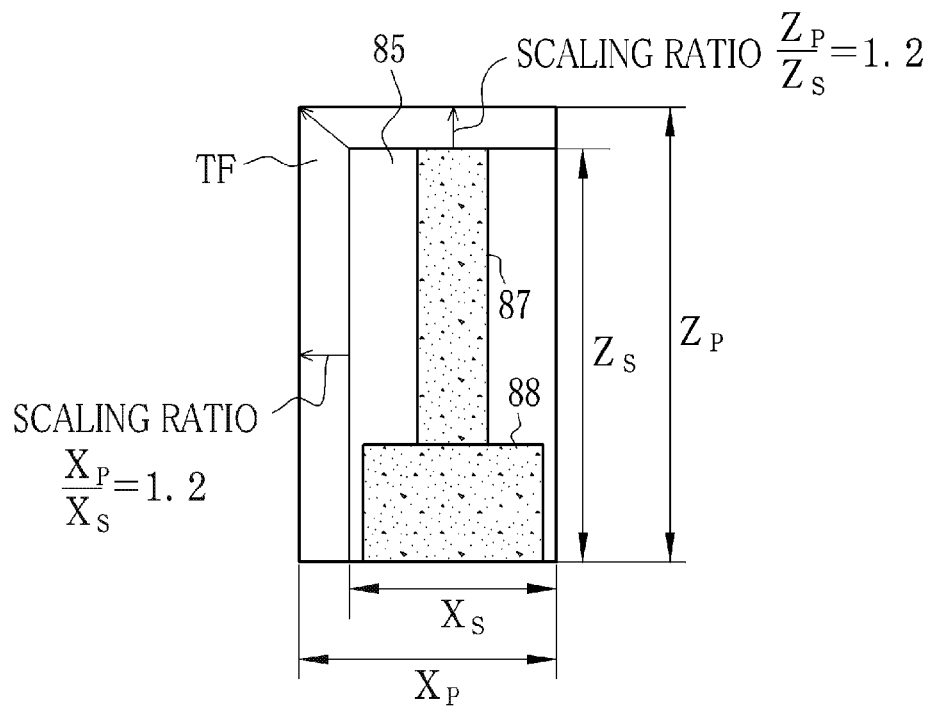
FULL SPINE IRRADIATION AREA MAP (BEFORE SCALING UP)
| IRRADIATION AREA | UPPER LEFT POINT | LOWER RIGHT POINT |
|---|---|---|
| SPINE | $X_1, 0$ | $X_3, Z_1$ |
| PELVIS | $X_2, Z_1$ | $X_4, Z_2$ |
FULL SPINE IRRADIATION AREA MAP (AFTER SCALING UP)
| IRRADIATION AREA | UPPER LEFT POINT | LOWER RIGHT POINT |
|---|---|---|
| SPINE | $1.2X_1, 0$ | $1.2X_3, 1.2Z_1$ |
| PELVIS | $1.2X_2, 1.2Z_1$ | $1.2X_4, 1.2Z_2$ |

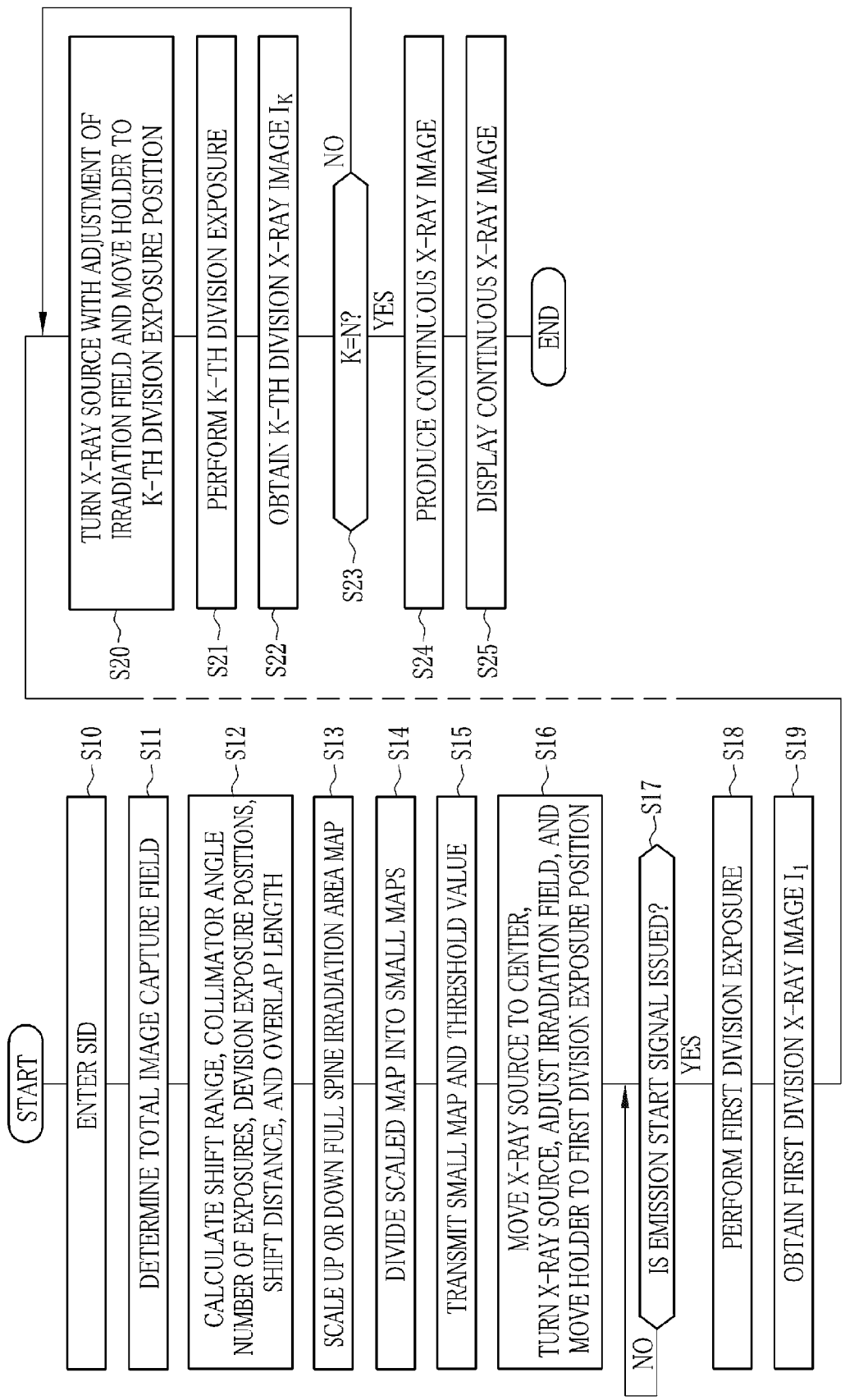

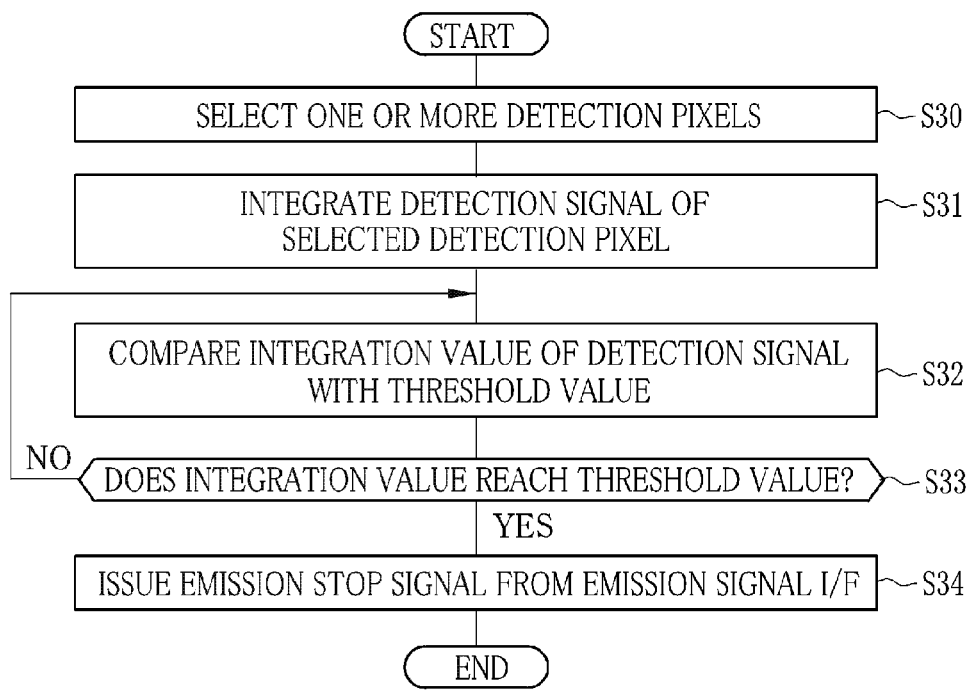

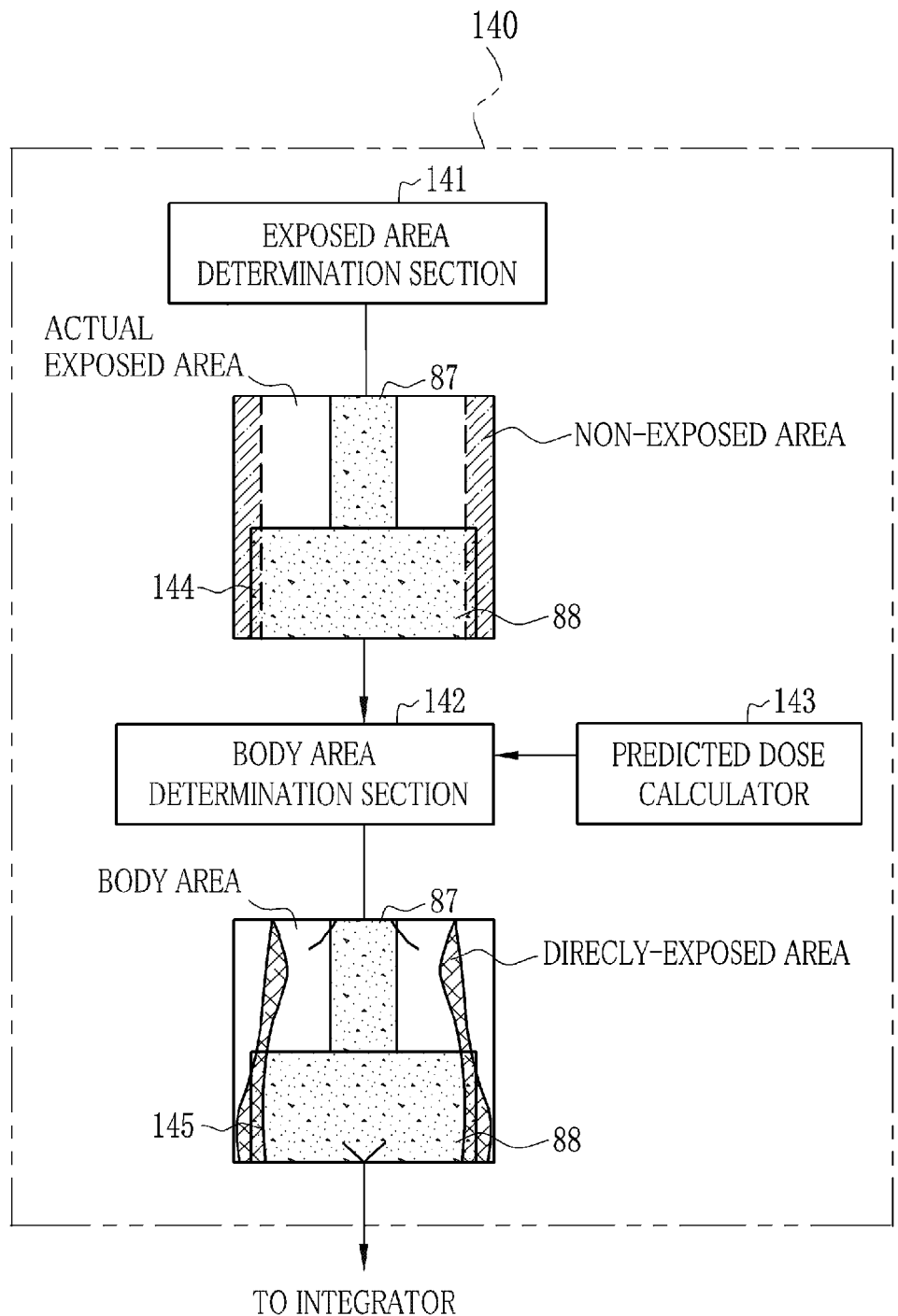

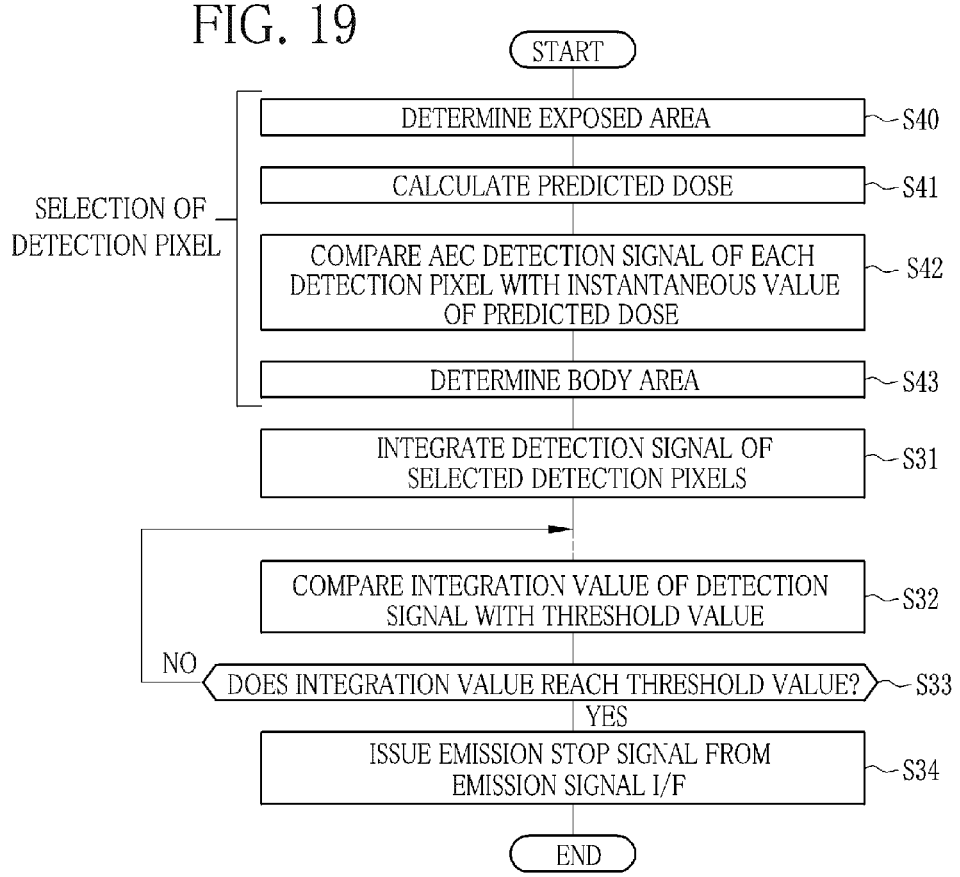
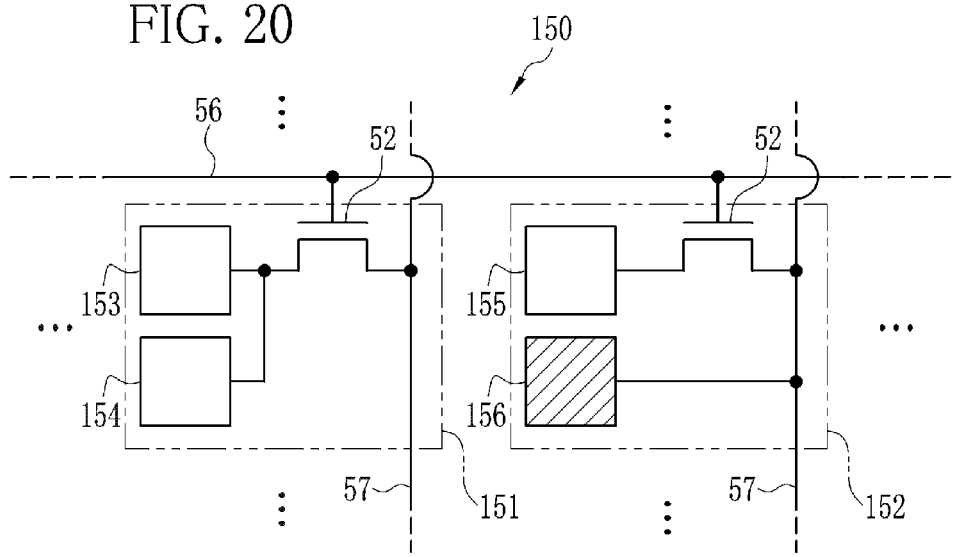

RADIATION IMAGING SYSTEM, METHOD FOR TAKING CONTINUOUS RADIOGRAPHIC IMAGE, AND RADIATION IMAGE DETECTING DEVICE

BACKGROUND OF THE INVENTION

1. Field of the Invention

The present invention relates to a radiation imaging system for taking a continuous radiographic image, a method for taking the continuous radiographic image, and a radiation image detecting device.

2. Description Related to the Prior Art

In a medical field, a radiation imaging system, for example, an X-ray imaging system using X-rays is widely known. The X-ray imaging system is constituted of an X-ray generation apparatus for generating the X-rays, and an X-ray image capturing apparatus for taking an X-ray image of a patient's body. The X-ray generation apparatus includes an X-ray source for emitting the X-rays to the body, a source controller for controlling the operation of the X-ray source, and an exposure switch for issuing an emission start signal of the X-rays. The X-ray image capturing apparatus includes an X-ray image detecting device for detecting the X-ray image based on the X-rays passed through the patient's body, and a console for controlling the operation of the X-ray image detecting device and applying various image processes to the X-ray image.

In recent years, the X-ray image detecting device that uses a flat panel detector (FPD) instead of an X-ray film or an imaging plate (IP) becomes widespread. The FPD has a matrix of pixels each of which accumulates signal charge by an amount corresponding to the amount of the X-rays incident thereon. The FPD accumulates the signal charge on a pixel-by-pixel basis, and converts the accumulated signal charge into a voltage signal by its signal processing circuit. Thereby, the FPD electrically detects the X-ray image, and outputs the X-ray image as digital image data.

An electronic cassette (portable X-ray image detecting device) that has the FPD contained in a flat and thin housing is in practical use. The electronic cassette is mounted not only on a specific imaging support, but also on an existing imaging support shareable between a film cassette and an IP cassette. Furthermore, the electronic cassette can be used while being put on a bed or held by the patient himself/herself, to take a radiograph of a body part that is hard to take with the stationary X-ray image detecting device. The electronic cassette is sometimes brought out from a hospital for use in bedside radiography of a home-care patient or in an outside accident or natural disaster site in an emergency.

There are some X-ray imaging systems having an automatic exposure control (AEC) function. Such systems have a dose detection sensor for detecting a dose of the X-rays passed through the patient's body. When an integration value of the X-ray dose detected by the dose detection sensor reaches a predetermined threshold value, the emission of the X-rays from the X-ray source is stopped.

Japanese Patent Laid-Open Publication No. 2002-000590 discloses an X-ray imaging system that carries out the AEC based on pixel signals from the FPD. This system obtains data that represents a pixel area (irradiation area) of the FPD corresponding to a body portion of interest (body portion to be imaged), that is, the addresses, size, and the like of the pixels corresponding to the body portion. The pixels to be used in the AEC are chosen in accordance with the body portion of interest.

According to Japanese Patent Laid-Open Publication No. 08-033621, in a mammography system, an outline of a breast is recognized in a preliminary exposure, and the size of the breast is calculated. The size of the pixel area (irradiation area) used in the AEC is varied in accordance with the size of the breast.

Besides taking a single exposure of a body part such as chest or abdomen with use of the fixed X-ray source and the fixed X-ray imaging detecting device, continuous radiography is known in which a plurality of exposures are taken while shifting the X-ray source and the X-ray image detecting device to obtain a continuous X-ray image. The continuous radiography is mostly used for observation of bones of the patient, such as skeletal age and bone curvature. In most cases, the continuous radiography is performed on a full spine extending from a clavicle to a pelvis, and on lower limbs extending from the pelvis to toes.

In the continuous radiography, a radiological technician firstly sets up a total image capture field in accordance with a body part to he imaged and the size of the patient i.e. standing height, sitting height, and an inseam. Based on the total image capture field and the size of the X-ray image detecting device (size of an imaging surface of a detection panel), the number of division exposures to be performed and division exposure positions, which are the positions of the X-ray source and X-ray image detecting device set in each division exposure, are calculated. After that, the division exposures are carried out. The division exposure positions are determined such that a plurality of division X-ray images obtained by the division exposures partly overlap one another. After completion of the division exposures, the plurality of division X-ray images are merged into the single continuous X-ray image by overlaying overlap areas of the division X-ray images.

In the continuous radiography, the total image capture field is large in size. Thus, for example, in the case of lower limb radiography, body thickness and the size of a directly-exposed area, in which no object exists, widely vary between waist and leg. Therefore, it is difficult to optimize the X-ray dose in each of the division exposure positions. Accordingly, in Japanese Patent Laid-Open Publication No. 2011-139761, an object is imaged by a digital camera, and an outline of the object is extracted. An AEC irradiation area is set up based on the outline in each division exposure. The pixels of the FPD are used as AEC sensors, and the AEC is performed in each division exposure based on signals from the pixels within the AEC irradiation area.

However, in the mammography system of the Japanese Patent Laid-Open Publication No. 08-033621, the preliminary exposure is carried out with the sole purpose of determining the irradiation area. In the system of the Japanese Patent Laid-Open Publication No. 2011-139761, the outline of the object is extracted from the image of the digital camera. Both the systems bring about increase in size and cost and a complicated and long-time process.

Also, in the Japanese Patent Laid-Open Publication No. 08-033621, the patient has to be exposed to an extra radiation dose in the preliminary exposure. In the Japanese Patent Laid-Open Publication No. 2011-139761, since the irradiation area is determined based on the outline of the object, the irradiation area includes not only an area of an important bone but also an area without the bone. Thus, the AEC may be performed improperly. If the patient puts on clothes or in plaster, the outline of the object becomes unclear, so the irradiation area possibly includes an area of no concern for diagnosis.

SUMMARY OF THE INVENTION

An object of the present invention is to provide a radiation imaging system, a method for taking a continuous radiographic image, and a radiation image detecting device that can easily determine an AEC irradiation area in continuous radiography.

To achieve the above and other objects, a radiation imaging system according to the present invention includes a radiation source, a radiation image detecting device, a plurality of dose detection sensors, a memory, a dose detection sensor selector, and an automatic exposure controller. The radiation source emits radiation to each of small image capture fields. The radiation image detecting device has a detection panel having an imaging surface having an arrangement of a plurality of pixels. The detection panel detects the radiation that has passed through a body part of the small image capture field to produce a division radiographic image. The plurality of dose detection sensors are substantially uniformly distributed in the imaging surface. Each dose detection sensor measures a radiation dose. The memory stores an irradiation area map that defines as an irradiation area an area for measuring the radiation dose in accordance with the body part to be imaged. The dose detection sensor selector selects one or more dose detection sensors belonging to the irradiation area based on the irradiation area map. The automatic exposure controller automatically controls a radiation exposure in each of the division exposures. The automatic exposure controller stops emission of the radiation from the radiation source in accordance with a measurement value obtained from a detection signal of the dose detection sensor selected by the dose detection sensor selector.

The measurement value is preferably an integration value of the detection signal of the selected dose detection sensor. If the integration value reaches a predetermined threshold value, the emission of the radiation is preferably stopped.

It is preferable that the radiation imaging system further includes a map scaling section for scaling up or down the irradiation area map so as to make the irradiation area map coincide with the total image capture field in size.

It is preferable that the radiation imaging system further includes a map dividing section that divides the irradiation area map scaled up or down by the map scaling section in accordance with the small image capture fields.

The irradiation area map may include a full spine irradiation area map for defining the irradiation areas corresponding to a pelvis and a spine, and a lower limb irradiation area map for defining the irradiation areas corresponding to the pelvis, knees, and ankles. The irradiation area map may include a first map for defining the irradiation area of complex shape and a second map for defining the irradiation area of simple shape.

The dose detection sensor selector may switch between the first map and the second map in accordance with the number of the division exposures or the small image capture field. The first map may define the irradiation area of inverse T shape corresponding to the pelvis and a part of the spine, and the second map may define the irradiation area being narrow and straight corresponding to the spine. The first map may define the irradiation area of π shape corresponding to the pelvis and a part of legs, and the second map may define the two straight irradiation areas corresponding to the legs. If the small image capture field to be first exposed includes the pelvis, the dose detection sensor selector may use the first map in a first exposure, and may use the second map in a second or later exposure.

The dose detection sensor selector may include an exposed area determination section for determining an actual exposed area based on an angle of a collimator of the radiation source and a positional relation between the radiation source and the radiation image detecting device. The dose detection sensor selector may select one or more of the dose detection sensors that are present within the actual exposed area determined by the exposed area determination section and belong to the irradiation area. The dose detection sensor selector may further include a predicted dose calculator and a body area determination section. The predicted dose calculator calculates an instantaneous value of a predicted dose received by a directly-exposed area of the imaging surface based on an operation condition of the radiation source and a positional relation between the radiation source and the radiation image detecting device. The radiation is directly incident upon the directly-exposed area without passing through the body part. The body area determination section determines a body area from a result of comparison between an instantaneous value of the detection signal of the dose detection sensor and the instantaneous value of the predicted dose. The dose detection sensor selector selects one or more of the dose detection sensors that are present within the body area and belong to the irradiation area.

It is preferable that the N number of small image capture fields partly overlap one another.

The plurality of pixels preferably include a normal pixel and a detection pixel. The normal pixel produces signal charge by an amount corresponding to the radiation dose, and accumulates the signal charge, and outputs the signal charge to a signal line through a switching element. The detection pixel is directly connected to the signal line, and functions as the dose detection sensor.

The radiation image detecting device may be an electronic cassette having the detection panel contained in a portable housing.

A method for taking a continuous radiographic image according to the present invention includes the steps of determining a total image capture field; dividing the total image capture field into a plurality of small image capture fields in accordance with a size of a detection panel of a radiation image detecting device; intermittently carrying out a plurality of division exposures, while relatively shifting a radiation source and the radiation image detecting device in accordance with each of the small image capture fields; in each of the division exposures, reading out an irradiation area map corresponding to the small image capture field, the irradiation area map defining an irradiation area; selecting one or more dose detection sensors for use in automatic exposure control based on the irradiation area map, the dose detection sensors being substantially uniformly distributed in an imaging surface of the detection panel; stopping emission of radiation from the radiation source in accordance with a measurement value obtained by a detection signal of the selected dose detection sensor; and producing a single continuous radiographic image from a plurality of division radiographic images obtained by the division exposures. The measurement value is an integration value of the detection signal of the selected dose detection sensor. If the integration value reaches a predetermined threshold value, the emission of the radiation is stopped.

A radiation image detecting device according to the present invention includes a detection panel, a plurality of dose detection sensors, a dose detection sensor selector, and a signal sender. The detection panel has an imaging surface having an arrangement of a plurality of pixels. Each pixel receives radiation from a radiation source through a body part and produces a signal. The dose detection sensors are substantially uniformly distributed in the imaging surface of the detection panel. Each dose detection sensor detects a radiation dose passed through the body part. The dose detection sensor selector selects one or more dose detection sensors belonging to an irradiation area determined in each of small image capture fields into which a total image capture field is divided, while division exposures of the small image capture fields are carried out to produce a continuous radiographic image. The signal sender measures the radiation dose with use of the selected dose detection sensor, and issues an emission stop signal based on an obtained measurement value to stop emission of the radiation from the radiation source in each of the division exposures. The measurement value is an integration value of a detection signal of the selected dose detection sensor. If the integration value reaches a predetermined threshold value, the emission of the radiation is stopped.

According to the present invention, the radiation imaging system has the irradiation area map that defines the irradiation area of each small image capture field. Thus, it is possible to easily select the dose detection sensors belonging to the irradiation area in the continuous radiography.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 3A is a perspective view that explains a setup of a total image capture field;

FIG. 3B is a projection view of FIG. 3A in a Z direction;

FIG. 3C is a projection view in the Z direction in a state of disposing an X-ray source at arbitrary height;

FIG. 9A is a table representing the full spine irradiation area map;

FIG. 9B is a table representing the lower limb irradiation area map;

FIG. 10 is a block diagram of the console;

FIG. 13 is an explanatory view of the function of a map scaling section;

FIG. 15 is a flowchart of a continuous radiography process;

FIG. 16 is a flowchart of an AEC process;

FIG. 18 is a block diagram showing a detection pixel selector of another embodiment;

FIG. 19 is a flowchart of an AEC process in the case of using the detection pixel selector of FIG. 18; and FIG. 20 is a schematic circuit diagram of an FPD of further another embodiment.

DESCRIPTION OF THE PREFERRED EMBODIMENTS

Figure 1:
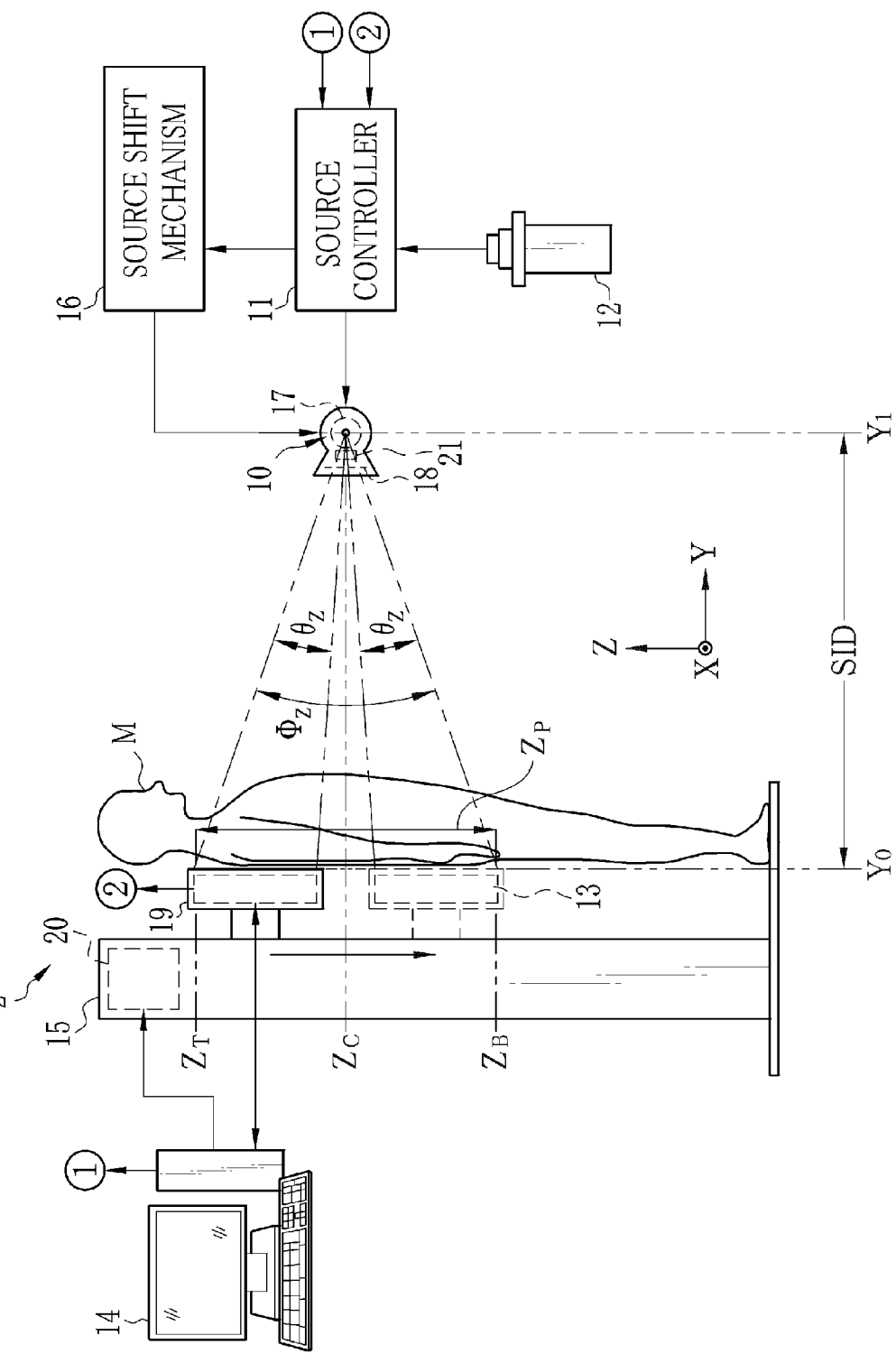
FIG. 1 is a schematic view of an X-ray imaging system.

As shown in FIG. 1, an X-ray imaging system 2 is constituted of an X-ray source 10, a source controller 11, an exposure switch 12, an electronic cassette 13, a console 14, and an upright imaging support 15. The source controller 11 controls the operation of the X-ray source 10. The exposure switch 12 commands the start of X-ray emission. The electronic cassette 13, being a radiation image detecting device, detects X-rays having passed through a patient M to output an X-ray image. The console 14 controls the operation of the electronic cassette 13, and supplies various image processes to the X-ray image. The upright imaging support 15 is used in taking a radiograph of the patient M in a standing position. The X-ray source 10 is moved and set in a desired orientation and position by a source shift mechanism 16 or the like.

The X-ray source 10 has an X-ray tube 17 for emitting the X-rays, and a collimator 18 for limiting an irradiation field of the X-rays emitted from the X-ray tube 17 in rectangular shape. The X-ray tube 17 has a cathode being a filament for emitting thermoelectrons, and an anode (target) for radiating the X-rays by collision of the thermoelectrons emitted from the cathode. The collimator 18 is composed of, for example, four X-ray shielding lead plates disposed on each side of a rectangle so as to form an irradiation opening in its middle through which the X-rays propagate. Under the control of the source controller 11, changing the positions of the lead plates can vary the size of the irradiation opening to limit the irradiation field.

The source controller 11 adjusts an angle range (hereinafter called collimator angle) of the X-rays from the collimator 18 in two directions, that is, a Z direction perpendicular to a floor and an X direction being a width direction of an imaging surface 41 (see FIG. 4) of an FPD 40 of the electronic cassette 13, such that an exposed area of the X-rays almost coincides with the imaging surface 41. In FIG. 1, "$\theta_Z$" represents the collimator angle in the Z (height) direction.

In continuous radiography, the source controller 11 controls the operation of the source shift mechanism 16 so that the X-ray source 10 turns in synchronization with a vertical shift of a holder 19 of the upright imaging support 15 in the Z direction set in division exposure positions. The source shift mechanism 16 includes an arm, a rail, and a driving source such as a motor. The arm hangs the X-ray source 10 from a ceiling in a shiftable and turnable manner in the Z direction. The arm is attached to the rail. The arm having the X-ray source 10 is moved along the rail in an XY direction (Y direction is a direction parallel to the floor of an examination room and orthogonal to the X direction). The source controller 11 controls the position and orientation of the X-ray source 10. Note that, the source controller 11 may be operated from an operation panel to change the position of the X-ray source 10. In the continuous radiography, after the determination of a total image capture field of the patient M, the X-ray source 10 is automatically shifted to height coinciding with the height of a center $Z_C$ in the Z direction.

Figure 2:
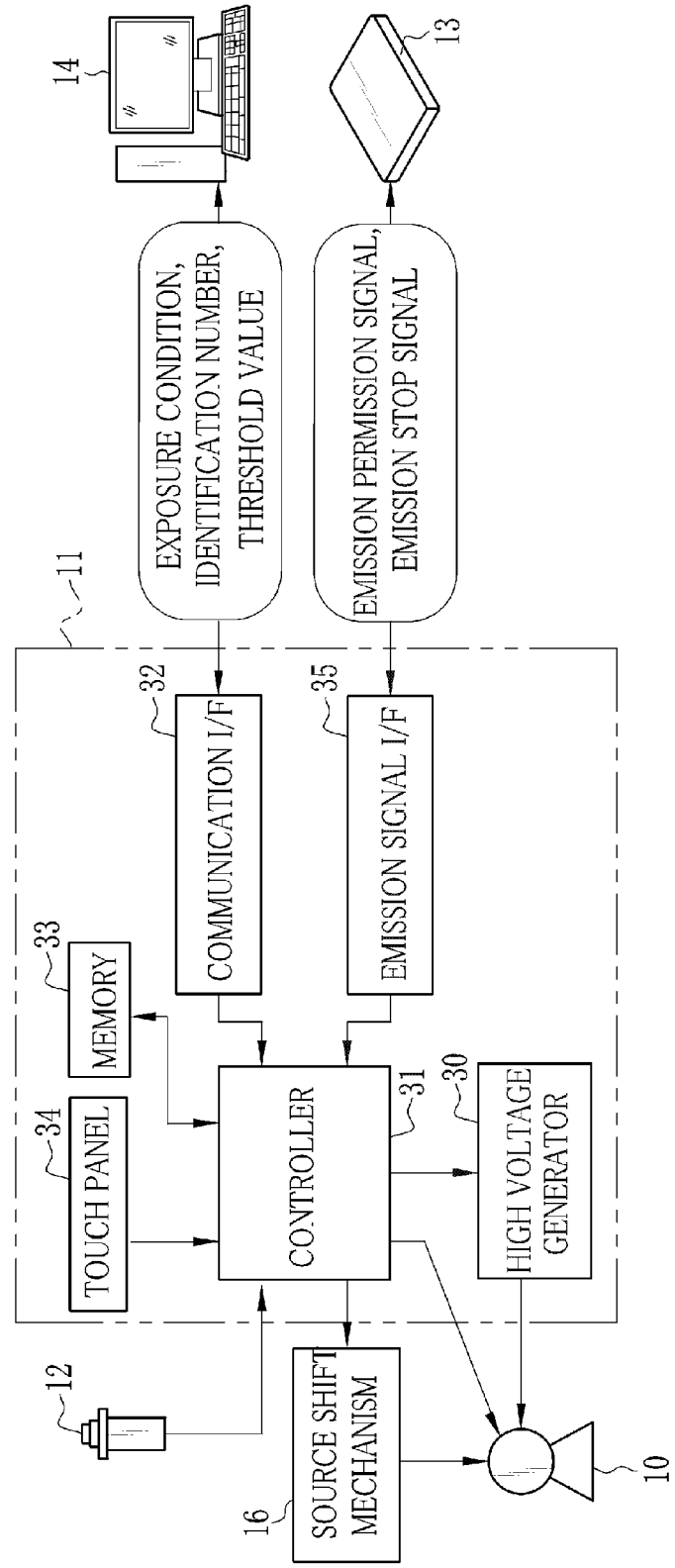
FIG. 2 is a block diagram of a source controller.

As shown in FIG. 2, the source controller 11 includes a high voltage generator 30, a controller 31, and a communication I/F 32. The high voltage generator 30 produces a high tube voltage by multiplying an input voltage using a transformer, and supplies drive power to the X-ray source 10 through a high voltage cable. The controller 31 controls the tube voltage for determining an energy spectrum of the X-rays from the X-ray source 10, a tube current for determining an X-ray irradiation amount per unit of time, and an X-ray irradiation duration. The communication I/F 32 mediates transmission and reception of various types of information and signals between the source controller 11 and the console 14.

To the controller 31, the exposure switch 12, a memory 33, and a touch panel 34 are connected. The exposure switch 12 is a two-step switch operated by a radiological technician. Upon a first press of the exposure switch 12, a warm-up start signal is issued to start warming up the X-ray source 10. Upon a second press, an emission start signal is issued to start emitting the X-rays from the X-ray source 10. These signals are inputted to the source controller 11 through a signal cable. The controller 31 starts supplying electric power from the high voltage generator 30 to the X-ray source 10 in response to the emission start signal from the exposure switch 12.

In the memory 33, several types of imaging conditions each of which includes the tube voltage, a product value (mAs value) of the tube current and the irradiation duration, and the like are stored in advance. The imaging conditions are manually inputted from the touch panel 34 by the radiological technician. The source controller 11 applies the X-rays based on the tube voltage and the product value (mAs value) of the set imaging condition. By automatic exposure control (AEC), an X-ray dose applied to the FPD 40 is measured. When the X-ray dose reaches a sufficient value, the X-ray emission is stopped even if the irradiation duration does not reach a set value. Note that, the imaging condition of the X-ray source 10 has the maximum product value or the maximum irradiation duration, in order to prevent a shortage of the X-ray dose caused by ending the X-ray emission before the judgment by the AEC.

An emission signal I/F 35 is connected to the electronic cassette 13 in the case of stopping the X-ray emission based on an output from detection pixels 65 (see FIG. 4) of the electronic cassette 13. In this case, upon reception of the warm-up start signal from the exposure switch 12, the controller 31 transmits a query signal to the electronic cassette 13 through the emission signal I/F 35. In response to the query signal, the electronic cassette 13 performs a preparation process, which includes completion of a reset process, start of a charge accumulation preparation process, and the like. After that, if the source controller 11 receives a emission permission signal, which is a response to the query signal, from the electronic cassette 13 at its emission signal I/F 35, and further receives the emission start signal from the exposure switch 12, the source controller 11 starts supplying the electric power from the high voltage generator 30 to the X-ray source 10. The electronic cassette 13 issues an emission stop signal upon detecting the predetermined X-ray dose. Upon receiving the emission stop signal through the emission signal I/F 35, the controller 31 stops supplying the electric power from the high voltage generator 30 to the X-ray source 10, to stop the X-ray emission.

As is widely known, the electronic cassette 13 is composed of the FPD 40 and a portable housing (not illustrated) containing the FPD 40. The housing of the electronic cassette 13 is in a rectangular flat box shape and approximately the same size as those of a film cassette and an IP cassette (also called CR cassette). In other words, the electronic cassette 13 is compatible with International Standard ISO4090:2001 in size and shape. Thus, the electronic cassette 13 can be mounted on an existing imaging support shareable between the film cassette and the IP cassette.

The electronic cassette 13 is detachably mounted on the holder 19 of the upright imaging support 15 in such a position that the imaging surface 41 of the FPD 40 is opposed to the X-ray source 10. In addition, the electronic cassette 13 can be used separately from the upright imaging support 15 in a state of being put on a bed under the patient's body or held by the patient M himself/herself.

In FIG. 1, the upright imaging support 15 is provided with a holder shift mechanism 20 that shifts the holder 19 perpendicularly to the Z direction without varying the orientation of the imaging surface 41 of the FPD 40 of the electronic cassette 13. The position (height) of the holder 19 is varied automatically by the holder shift mechanism 20 under the control of the console 14 or manually by the radiological technician, so the position of the electronic cassette 13 is varied in accordance with small image capture fields into which the total image capture field is divided.

The X-ray source 10 is provided with a laser light source 21. The laser light source 21 is turned on when determining the total image capture field of the patient M. The laser light source 21 applies two linear laser light beams parallel to the X and directions, respectively, to the upright imaging support 15.

In the continuous radiography, the total image capture field is determined at the start. To determine the total image capture field, the radiological technician stands the patient M in a predetermined position in front of the upright imaging support 15, and turns on the laser light source 21 by operation of the touch panel 34 of the source controller 11. Then, as shown in FIGS. 3A and 3B, to determine the length of the total image capture field TF in the Z direction, the X-ray source 10 is set by operation of the source shift mechanism 16 at height that coincides with a top end $Z_T$ of the total image capture field TF. After that, the X-ray source 10 is turned downward in the direction by operation of the touch panel 34 such that the horizontal linear laser light beam coincides with a bottom end $Z_B$ of the total image capture field TF. In a like manner, to determine the width $X_P$ of the total image capture field TF in the X direction, the X-ray source 10 is turned from side to side by operation of the touch panel 34 while emitting the vertical linear laser light beam. Note that, the X-ray source 10 is turned in the X direction equiangularly ($\phi_X/2$). At this time, the height ($Z_T$) in the Z direction and turn angles $\phi_X$ and $\phi_Z$ of the X-ray source 10 are detected with the use of a potentiometer contained in the source shift mechanism 16. The detection result of the potentiometer is transmitted from the source controller 11 to the console 14 by operation of the touch panel 34. Note that, in FIG. 1, $Z_P$ represents the length of the total image capture field TF in the full spine radiography, and extends from a neck to a waist (pelvis) of the patient M over an entire upper body. The total image capture field TF varies depending on a body part to be imaged and the height of the patient M.

As described above, the height of the X-ray source 10 is made coincide with the top end $Z_T$ of the desired total image capture field and then is turned downward in the Z direction to the bottom end $Z_B$. However, after determination of the bottom end $Z_B$, the X-ray source 10 may be turned upward in the Z direction to determine the top end $Z_T$. Also, as shown in FIG. 3C, the X-ray source 10 may be disposed at arbitrary height, and turned upward in the Z direction to determine the top end $Z_T$ and downward to determine the bottom end $Z_B$. The total image capture field TF may be determined based on the height and turn angles $\phi'_Z$ and $\phi''_Z$ of the X-ray source 10.

Figure 4:
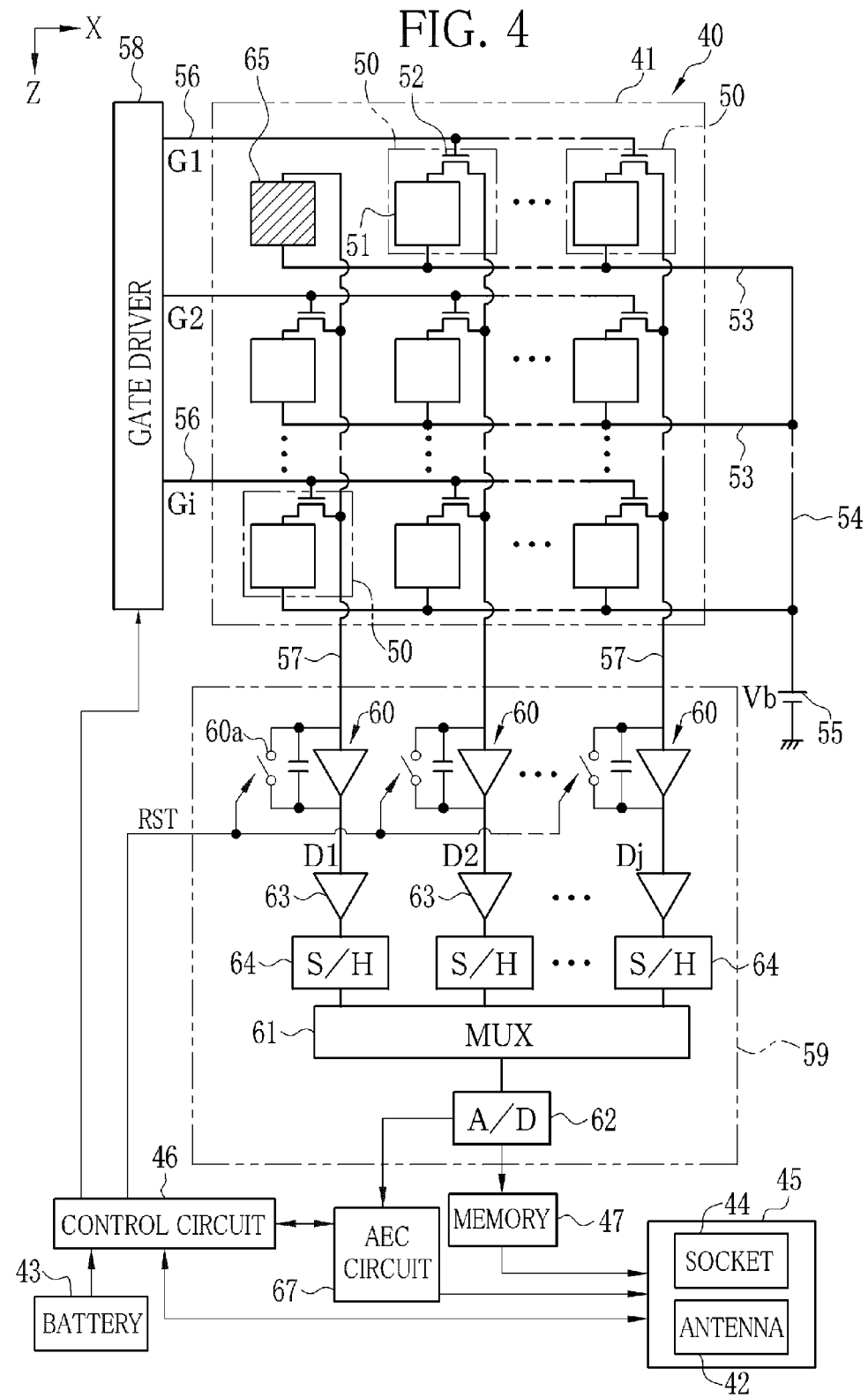
FIG. 4 is a block diagram of an electronic cassette.

In FIG. 4, the electronic cassette 13 including an antenna 42 and a battery 43 can establish wireless communication with the console 14. The antenna 42 transmits and receives a radio wave for use in the wireless communication to and from the console 14. The battery 43 supplies electric power to the electronic cassette 13. The battery 43 is small enough to be contained in the slim electronic cassette 13. The battery 43 can be taken out of the electronic cassette 13 and mounted on a specific cradle for recharging. The electronic cassette 13 may be recharged by a wireless power feeder.

In addition to the antenna 42, the electronic cassette 13 is provided with a socket 44. The socket 44, which is for establishing wired communication with the console 14, is used when the wireless communication between the electronic cassette 13 and the console 14 is disabled due to a shortage of the battery 43 or the like. Connecting a cable of the console 14 to the socket 44 enables the wired communication with the console 14. Through the cable, the console 14 may supply electric power to the electronic cassette 13. The antenna 42 and the socket 44 are provided in a communication circuit 45. The communication circuit 45 mediates various types of information and signals including image data between the antenna 42 or the socket 44 and a control circuit 46, and between the antenna 42 or the socket 44 and a memory 47.

The FPD 40 has the imaging surface 41, which has a TFT active matrix substrate and a plurality of pixels arranged on the TFT active matrix substrate. The pixels (including normal pixels 50 and detection pixels 65) accumulate signal charge by an amount corresponding to the amount of the X-rays incident thereon. The plurality of pixels are arranged into a two-dimensional matrix with i rows (Z, direction) and j columns (X direction) at a predetermined pitch.

The FPD 40 is of an indirect conversion type, having a scintillator (phosphor, not illustrated) for converting the X-rays into visible light. The pixels perform photoelectric conversion of the visible light produced by the scintillator. The scintillator is made of CsI (cesium iodide), GOS (gadolinium oxysulfide), or the like, and is opposed to the imaging surface 41 having the matrix of the pixels. Note that, the scintillator and the FPD 40 may adopt either a PSS (penetration side sampling) method or an ISS method. In the PSS method, the scintillator and the FPD 40 are disposed in this order from an X-ray incident side. In the ISS method, the scintillator and the FPD 40 are disposed in reverse order. Note that, a direct conversion type FPD, which has a conversion layer (amorphous selenium or the like) for directly converting the X-rays into electric charge, may be used instead.

The pixels include the normal pixels 50 for detecting the X-ray image and the detection pixels 65 for use in the AEC. Each normal pixel 50 is composed of a photodiode 51, a capacitor (not shown), and a thin film transistor (TFT) 52. The photodiode 51 being a photoelectric conversion element produces electric charge (electron and hole pairs) upon entry of the visible light. The capacitor accumulates the electric charge produced by the photodiode 51. The TFT 52 functions as a switching element.

The photodiode 51 is composed of a semiconducting layer (of a PIN type, for example) for producing the electric charge, and upper and lower electrodes disposed on the top and bottom of the semiconducting layer. The lower electrode of the photodiode 51 is connected to the TFT 52. The upper electrode of the photodiode 51 is connected to a bias line 53. The number of the bias lines 53 coincides with the number of rows (i rows) of the pixels. All the i bias lines 53 are connected to a bias power source 55 through a bus 54. The bias power source 55 applies a bias voltage Vb to the upper electrodes of the photodiodes 51 through the bus 54 and the bias lines 53. Since the application of the bias voltage Vb produces an electric field in the semiconducting layer, the electric charge (electron and hole pairs) produced in the semiconducting layer by the photoelectric conversion is attracted to the upper and lower electrodes, one of which has positive polarity and the other has negative polarity. Thereby, the electric charge is accumulated in the capacitor.

A gate electrode of the TFT 52 is connected to a scan line 56. A source electrode of the TFT 52 is connected to a signal line 57, and a drain electrode is connected to the photodiode 51. The scan lines 56 and the signal lines 57 are routed into a lattice. The number of the scan lines 56 coincides with the number of the rows (i rows) of the pixels. The number of the signal lines 57 coincides with the number of the columns (j columns) of the pixels. All the scan lines 56 are connected to a gate driver 58, and all the signal lines 57 are connected to a signal processing circuit 59.

The gate driver 58 drives the TFTs 52 to make the FPD 40 carry out a charge accumulation operation in which each normal pixel 50 accumulates the signal charge by an amount corresponding to the amount of the X-rays incident thereon, a readout operation (real discharge operation) in which the signal charge is read out from the normal pixels 50 after the X-ray emission, and a reset operation (idle discharge operation) performed immediately before the X-ray emission. The control circuit 46 controls start timing of each of the above operations carried out by the gate driver 58.

In the charge accumulation operation, while every TFT 52 is turned off, every normal pixel 50 accumulates the signal charge. In the readout operation, the gate driver 58 successively issues gate pulses G1 to Gi each of which drives the TFTs 52 of the same row at a time. Thereby, the scan lines 56 are activated one by one so as to turn on the TFTs 52 connected to the activated scan line 56 on a row-by-row basis. Upon turning on the TFT 52, the signal charge accumulated in the capacitor of the normal pixel 50 is read out to the signal line 57, and inputted to the signal processing circuit 59.

Dark charge occurs in the semiconducting layer of the photodiode 51 irrespective of the presence or absence of entry of the X-rays. Due to the application of the bias voltage Vb, the dark charge is accumulated in the capacitor. The dark charge occurring in the normal pixels 50 becomes noise of the image data, and therefore the reset operation is carried out to remove the dark charge. In other words, the reset operation is an operation in which unnecessary charge e.g. the dark charge accumulated in the normal pixels 50 is discharged through the signal lines 57.

The reset operation adopts a sequential reset method, for example, by which the normal pixels 50 are reset on a row-by-row basis. In the sequential reset method, as in the case of the readout operation of the signal charge, the gate driver 58 successively issues the gate pulses G1 to Gi to the scan lines 56, to turn on the TFTs 52 of the normal pixels 50 on a row-by-row basis. While the TFT 52 is turned on, the dark charge flows from the normal pixel 50 through the signal line 57 into an integration amplifier 60. In the reset operation, in contrast to the readout operation, a multiplexer (MUX) 61 does not read out the electric charge accumulated in the integration amplifiers 60. In synchronization with the issue of each gate pulse G1 to Gi, the control circuit 46 outputs a reset pulse RST to reset the integration amplifiers 60.

Instead of the sequential reset method, a parallel reset method or an all pixels reset method may be used. In the parallel reset method, a plurality of rows of pixels are grouped together, and sequential reset is carried out in each group, so as to concurrently discharge the dark charge from the rows of the number of the groups. In the all pixels reset method, the gate pulse is inputted to every row to concurrently discharge the dark charge from every normal pixel 50. Adoption of the parallel reset method and the all pixels reset method can reduce time required for the reset operation.

The signal processing circuit 59 is provided with the integration amplifiers 60, the MUX 61, an A/D converter 62, and the like. One integration amplifier 60 is connected to each signal line 57. The integration amplifier 60 includes an operational amplifier and a capacitor connected between input and output terminals of the operational amplifier. The signal line 57 is connected to one of two input terminals of the operational amplifier. The other input terminal of the operational amplifier is connected to a ground (GND). The integration amplifier 60 integrates the signal charge inputted from the signal line 57, and converts the signal charge into a voltage signal D1 to Dj, and outputs the voltage signal D1 to Dj. The output terminal of the integration amplifier 60 of every column is connected to the MUX 61 through another amplifier 63 and a sample holder (S/H) 64. An output of the MUX 61 is connected to the A/D converter 62.

The MUX 61 successively chooses one of the plurality of integration amplifiers 60 connected in parallel, and inputs the voltage signal Dl to Di outputted from the chosen integration amplifier 60 to the A/D converter 62. The A/D converter 62 converts the inputted voltage signals D1 to Dj into digital data, and outputs the digital data to the memory 47 contained in the electronic cassette 13. Note that, another amplifier may be provided between the MUX 61 and the A/D converter 62.

After the MUX 61 reads out from the integration amplifiers 60 the voltage signals D1 to Dj of one row, the control circuit 46 outputs the reset pulse RST to the integration amplifiers 60 to turn on reset switches 60a of the integration amplifiers 60. Thus, the signal charge of one row accumulated in the integration amplifiers 60 is reset. Upon the reset of the integration amplifiers 60, the gate driver 58 outputs the gate pulse of the next row to start reading out the signal charge from the normal pixels 50 of the next row. Successively repeating this operation, the signal charge is read out from the normal pixels 50 of every row.

After completion of the readout from every row, the image data representing the X-ray image of one frame is written to the memory 47. This image data is read out from the memory 47, and outputted to the console 14 through the communication circuit 45. Thereby, the electronic cassette 13 detects the X-ray image of the patient M.

Upon receiving the query signal from the controller 31 of the source controller 11, the control circuit 46 performs the reset operation of the FPD 40, and sends the emission permission signal back to the source controller 11. After that, upon receiving the emission start signal, the control circuit 46 stops the reset operation and starts the charge accumulation operation of the FPD 40.

The FPD 40 has not only the normal pixels 50 connected to the signal line 57 through the TFT 52, but also the plurality of detection pixels 65 connected to the signal line 57 without through the TFT 52 in its imaging surface 41. The detection pixels 65 are used for detecting the X-ray dose incident upon the imaging surface 41 through the patient M. The detection pixels 65 function as an irradiation start detection sensor, an irradiation end detection sensor, and an AEC sensor (dose detection sensor). The number of the detection pixels 65 occupies about several percent of a total pixel number of the imaging surface 41.

Figure 5:
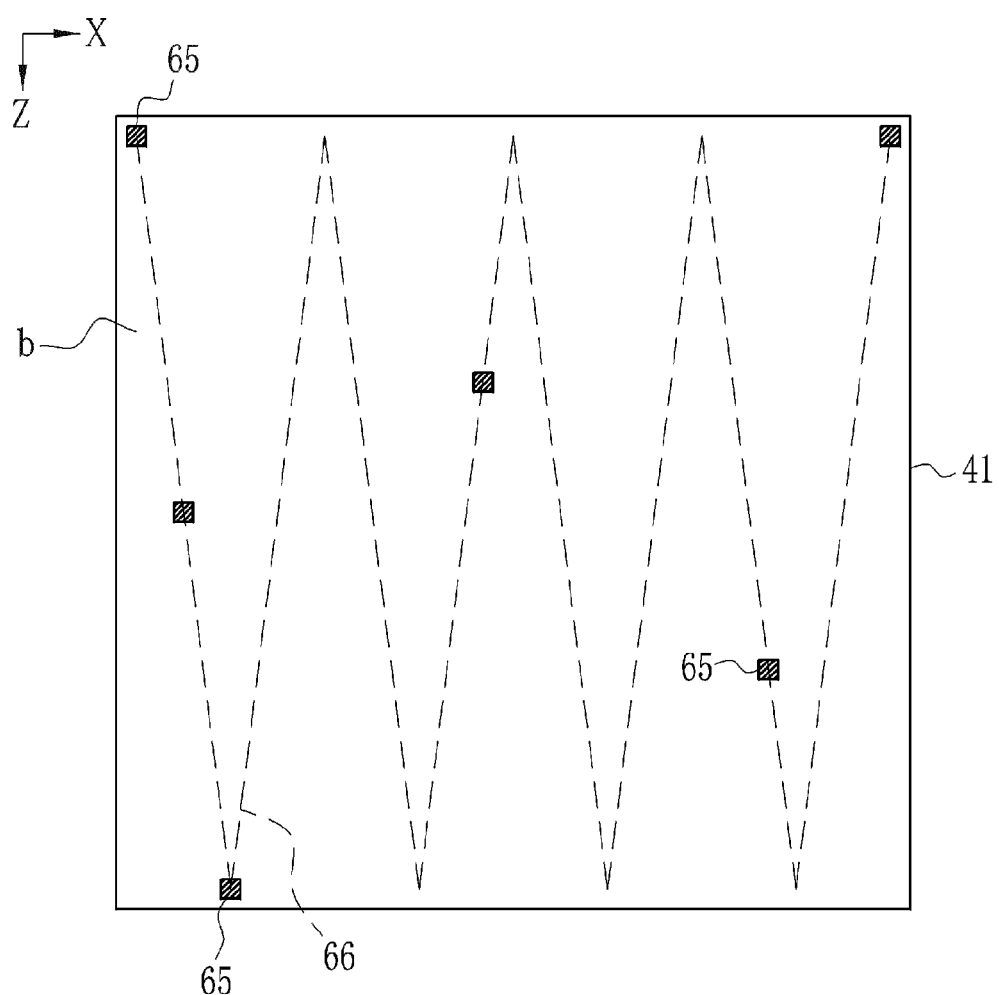
FIG. 5 is an explanatory view of distribution of detection pixels in an imaging surface.

As shown in FIG. 5, the detection pixels 65 are disposed along a zigzag line symmetric with respect to the center of the imaging surface 41 as shown by a dotted line so as to be almost uniformly distributed in the imaging surface 41. For example, one detection pixel 65 is laid out every two to three signal lines 57, and two or more detection pixels 65 are not laid out in the single signal line 57. The positions of the detection pixels 65 are known in manufacturing the FPD 40, and the FPD 40 has a nonvolatile memory (not shown) that stores the position (coordinates) of every detection pixel 65 in advance. Note that, the disposition of the detection pixels 65 shown in FIG. 5 is just an example, and is appropriately changeable.

Since the detection pixel 65 is connected to the signal line 57 directly without through the TFT 52, the signal charge produced in the detection pixel 65 immediately flows into the signal line 57. For example, the detection pixel 65 continues outputting the signal charge, even if the normal pixels 50 disposed in the same row as that of the detection pixel 65 are in the middle of the charge accumulation operation. Thus, the electric charge produced in the detection pixel 65 always flows into the integration amplifier 60 in the signal line 57 connected to the detection pixel 65. During the charge accumulation operation of the FPD 40, the integration amplifier 60 integrates the electric charge from the detection pixel 65 and outputs an integration value as a voltage value (AEC detection signal). This voltage value is fetched at predetermined sampling intervals, and is outputted to the A/D converter 62 through the MUX 61.

In FIG. 4, an AEC circuit 67 is controlled by the control circuit 46. The AEC circuit 67 fetches an AEC detection signal that is converted into a digital signal by the A/D converter 62.

Figures 6, 7:
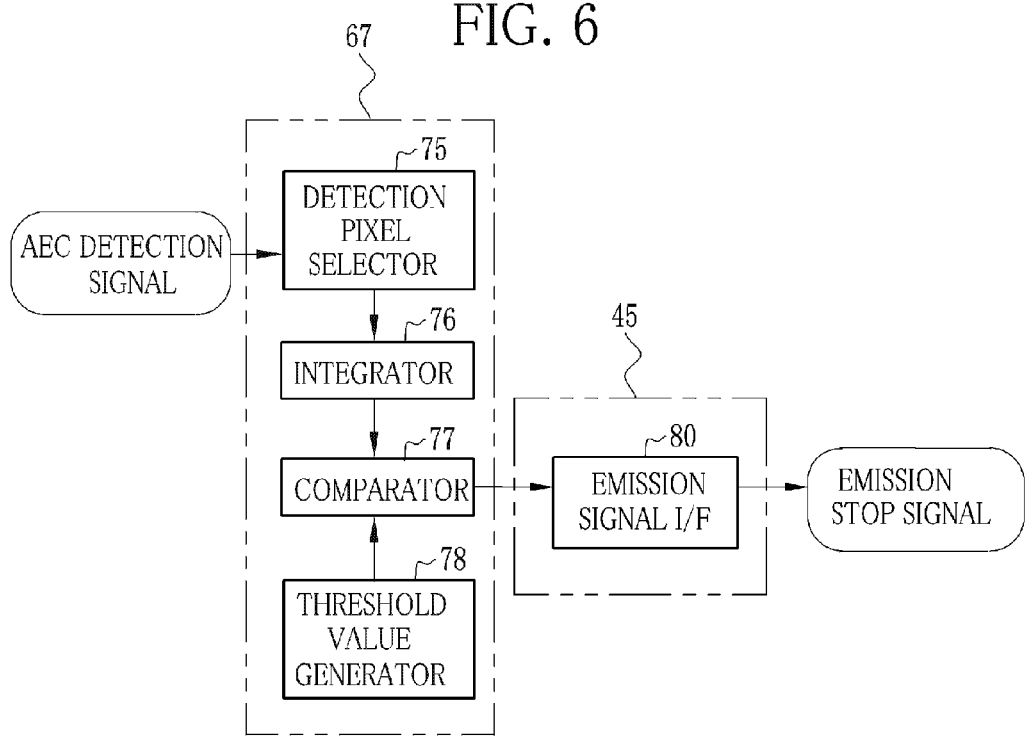
FIG. 6 is a block diagram of an AEC circuit and communication circuit of the electronic cassette.
FIG. 7 is a table of imaging conditions set up in a console.

As shown in FIG. 6, the AEC circuit 67 includes a detection pixel selector (dose detection sensor selector) 75, an integrator 76, a comparator 77, and a threshold value generator 78. The detection pixel selector 75 selects which detection pixels (dose detection sensors) 65 to use in the AEC (automatic exposure control) in each division exposure, out of the plurality of detection pixels 65 distributed in the imaging surface 41, based on irradiation area data from the console 14. The integrator 76 integrates the AEC detection signal from each detection pixel 65 selected by the detection pixel selector 75 during sampling by the S/H 64. The comparator 77 starts monitoring an integration value of the integrator 76, when the start of X-ray emission is detected. The comparator 77 compares the integration value with an emission stop threshold value provided by the threshold value generator 78. If the integration value reaches the threshold value, the comparator 77 issues an emission stop signal. The integration value is used as a measurement signal obtained from each AEC detection signal, but an average value, a maximum value, or a mode value of the AEC detection signals may be used instead, and emission stop timing may be judged from the level of this measurement value.

The communication circuit 45 includes an emission signal I/F 80 in addition to the antenna 42 and the socket 44 as described above. To the emission signal I/F 80, the emission signal I/F 35 of the source controller 11 is connected. The emission signal I/F 80 performs reception of the query signal, transmission of the emission permission signal in response to the query signal, and transmission of an output i.e. the emission stop signal from the comparator 77.

The console 14 is communicatably connected to the electronic cassette 13 in a wired or wireless method, to control the operation of the electronic cassette 13. To be more specific, the console 14 transmits the imaging condition to the electronic cassette 13 to set up a signal processing condition (e.g. gain of an amplifier for multiplying voltage corresponding to the accumulated signal charge) of the FPD 40. Additionally, the console 14 turns on and off the electronic cassette 13, and puts the electronic cassette 13 into a power saving mode, an exposure preparation mode, and the like.

The console 14 applies various image processes such as offset correction, gain correction, and defect correction to the X-ray image data transmitted from the electronic cassette 13. In the defect correction, pixel values of the row having the detection pixel 65 are interpolated using the pixel values of the adjacent row without having the detection pixel 65. Referring to FIG. 10, the X-ray image after subjected to the image processes is displayed on a monitor 104 of the console 14, and its data is written to a storage device 102 and a memory 101 of the console 14, or an image storage server connected to the console 14 through a network.

To the console 14, an examination order including information about sex and age of the patient, a body part to be imaged, an examination purpose, and the like is inputted from an input device 105 such as a keyboard. This examination order is displayed on the monitor 104. The examination order is inputted from an external system e.g. HIS (hospital information system) or RIS (radiography information system) that manages patient data and examination data related to radiography, or inputted manually by the radiological technician. The examination order includes the body part to be examined e.g. head, chest, abdomen, full spine, lower limbs, and the like, and an imaging direction e.g. anterior, medial, diagonal, PA (X-rays are applied from a posterior direction), and AP (X-rays are applied from an anterior direction). The radiological technician confirms the contents of the examination order on the monitor 104, and inputs the imaging condition corresponding to the contents of the examination order from the input device 105 through an operation screen displayed on the monitor 104.

As shown in FIG. 7, the console 14 has one imaging condition set for each body part. The imaging condition includes an irradiation area map used for selection of the detection pixels 65, the emission stop threshold value used in comparison with the integration value of the AEC detection signal of the selected detection pixels 65 in order to judge the stop of X-ray emission, and the like. This information about the imaging condition is stored in the storage device 102. Note that, FIG. 7 shows only two body parts of "full spine" and "lower limbs" for use in the continuous radiography, but in actual fact, the imaging conditions of the other body parts such as chest AP, chest PA, head, and abdomen are stored too.

Figure 8:
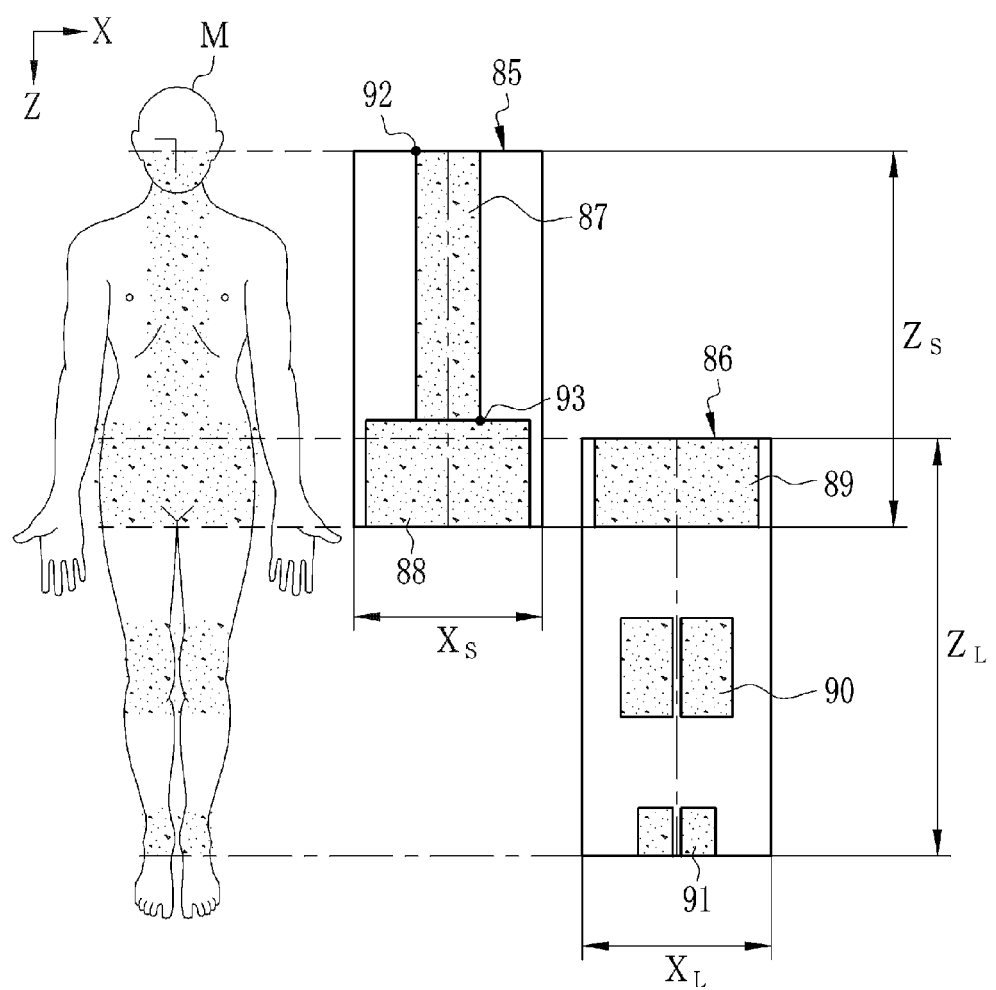
FIG. 8 is an explanatory view of a full spine irradiation area map and a lower limb irradiation area map.

As shown in FIG. 8, a full spine irradiation area map 85 used in full spine radiography has irradiation areas 87 and 88 that cover a spine and a pelvis, respectively, extending from the chest to the abdomen of the patient M. A lower limb irradiation area map 86 used in lower limb radiography has irradiation areas 89 to 91 that cover the pelvis, keens, and ankles, respectively. Both the full spine irradiation area map 85 and the lower limb irradiation area map 86 are in a rectangle shape. The full spine irradiation area map 85 has a width of $X_S$ and a length of $Z_S$. The lower limb irradiation area map 86 has a width of $X_L$ ($=X_S$) and a length of $Z_L$. These widths and lengths are determined based on the body size of an average adult male. Each of the irradiation areas 87 to 91 is symmetric with respect to a body axis of the patient M.

As shown in FIGS. 9A and 9B, each irradiation area map 85, 86 is concretely represented by XZ plane coordinates with their origin at an upper left point. Each of the irradiation areas 87 to 91 is represented by coordinates of an upper left start point and a lower right endpoint diagonal to each other. For example, as for the irradiation area 87 of the spine shown in FIG. 8, the coordinates of a start point 92 is ($X_1$, 0), and the coordinates of an end point 93 is ($X_3$, $Z_1$). Since the irradiation areas 87 to 91 are rectangular, the layout of the irradiation areas 87 to 91 in the irradiation area maps 85 and 86 is known from the coordinates of the start points and the end points. The data of the irradiation area map is not limited to above, but may be data that represents whether or not each plane coordinate corresponds to the irradiation area, for example. The shape of the irradiation area is not limited to rectangle, but may be round or ellipsoidal. In this case, the irradiation area map has information of the coordinates of a center of the round or ellipse, and the radius of the round or the length of major and minor axes of the ellipse.

As shown in FIG. 10, the console 14 is composed of a computer having a CPU 100, the memory 101, the storage device 102, a communication I/F 103, the monitor 104, and the input device 105. These components are connected to each other via a data bus 106.

The storage device 102 is a hard disk drive (HDD), for example. The storage device 102 stores control programs and application programs 107. Running the application programs 107 makes the console 14 perform various functions related to the radiography, such as a display process of the examination order and the X-ray image, the image processes of the X-ray image, and setup of the imaging condition.

The memory 101 is a work memory used when the CPU 100 executes. The CPU 100 loads the control programs stored on the storage device 102 into the memory 101, and runs the programs for centralized control of the computer. The communication I/F 103 functions as a network interface for performing wireless or wired transmission control from/to an external device such as the RIS, the HIS, the image server, and the electronic cassette 13. The input device 105 includes a keyboard and a mouse, or a touch panel integrated with the monitor 104. The input device 105 is operated in a setup of the imaging condition, entry of source-to-image distance (SID, see FIG. 1) from a position $Y_0$ of the imaging surface 41 of the FPD 40 to a position $Y_1$ of the focus of the X-ray tube 17, and the like.

Figure 11:
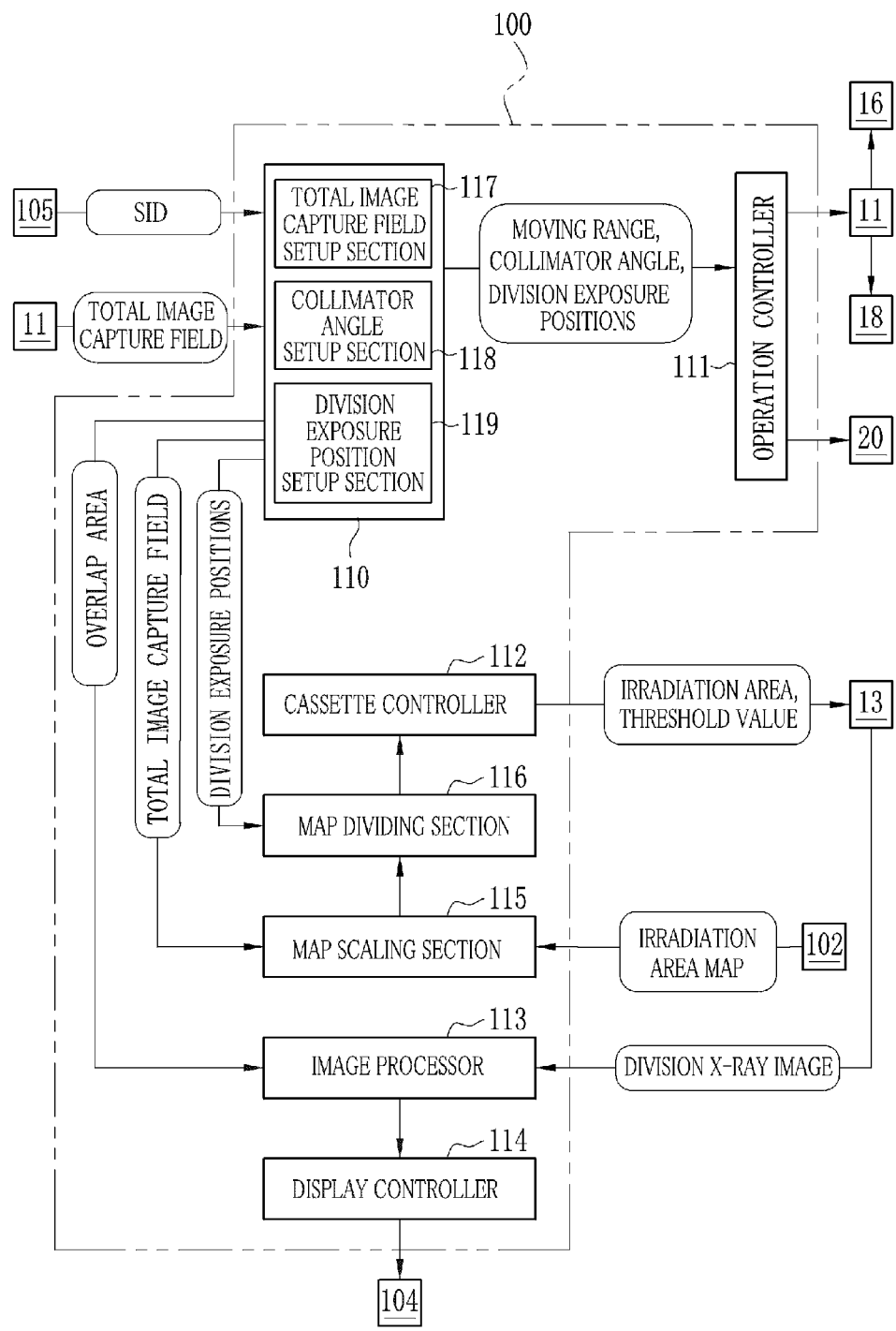
FIG. 11 is a block diagram showing the function of the console.

As shown in FIG. 11, by running the application programs 107 and choosing the continuous radiography, the CPU 100 of the console 14 functions as an operation condition setup section 110, an operation controller 111, a cassette controller 112, an image processor 113, a display controller 114, a map scaling section 115, and a map dividing section 116. The operation condition setup section 110 includes a total image capture field setup section 117 for setting a shift range of the holder 19 and a turn angle of the X-ray source 10, a collimator angle setup section 118 for setting a collimator angle, and a division exposure position setup section 119 for setting division exposure positions within the above shift range. The operation condition setup section 110 sets up various terms of the operation condition in the continuous radiography. The operation controller 111 operates the source shift mechanism 16 and the collimator 18 through the source controller 11, and operates the holder shift mechanism 20 in accordance with the set operation condition. The image processor 113 applies various image processes such as the offset correction, the gain correction, and the defect correction, and merges division X-ray images of the small image capture fields into a single continuous X-ray image. The display controller 114 displays on the monitor 104 the continuous X-ray image, an operation menu of the radiography, and the like.

The total image capture field setup section 117 calculates the width $X_P$ and length $Z_P$ of the total image capture field based on the SID inputted from the input device 105 and a detection result (top end $Z_T$ and turn angles $\phi_X$ and $\phi_Z$) of the potentiometer when determining the total image capture field using the laser light source 21. More specifically, the following expressions (1-1) and (1-2) are calculated (see FIG. 3).

$$X_P = 2 \times SID \times \tan(\phi_X/2) \tag{1-1}$$

$$Z_P = SID \times \tan \phi_Z \tag{1-2}$$

From this calculation results, the bottom end $Z_B$ and the center $Z_C$ of the total image capture field are obtained. The total image capture field setup section 117 determines the shift range of the holder 19 based on the top end $Z_T$ and the bottom end $Z_B$ of the total image capture field in the Z direction, and sets the X-ray source 10 at the center $Z_C$ in the continuous radiography. In the case of the full spine radiography, the holder shift mechanism 20 shifts the holder 19 from a shift start position set at the bottom end $Z_B$ to a shift end position set at the top end $Z_T$. In the case of the lower limb radiography, on the contrary, the top end $Z_T$ is set at a shift start position, and the bottom end $Z_B$ is set at a shift end position. Accordingly, the pelvis is first exposed in both the full spine radiography and the lower limb radiography.

The total image capture field setup section 117 calculates a turn angle range $\Phi_Z$ (see FIG. 1) of the X-ray source 10 disposed at the center $Z_C$ of the total image capture field in the Z direction by the following expression (2).

$$\Phi_Z = 2 \times \tan^{-1}\{(Z_P/2)/SID\} \tag{2}$$

The source shift mechanism 16 changes the turn angle $\phi_Z$ of the X-ray source 10 in the Z direction to the turn angle range $\Phi_Z$ so as to make the turn of the X-ray source 10 coincide with the shift of the holder 19.

The collimator angle setup section 118 calculates the collimator angle in the continuous radiography based on the SID inputted from the input device 105, the size of the imaging surface 41 of the FPD 40 (known in advance), and the width $X_P$ of the total image capture field. If FOV (see FIG. 12) represents the length of the imaging surface 41 in the Z direction, a collimator angle $\theta_Z$ relative to the Z direction is calculated by the following expression (3-2). In a like manner, a collimator angle $\theta_X$ relative to the X direction is calculated by the following expression (3-1) in which $X_P$ is substituted for FOV of the expression (3-2).

$$\theta_X = 2 \times \tan^{-1}\{(X_P/2)/SID\} \tag{3-1}$$

$$\theta_Z = 2 \times \tan^{-1}\{(FOV/2)/SID\} \tag{3-2}$$

The collimator angle $\theta_X$ calculated by the above expression (3-1) is commonly used in each division exposure position. On the other hand, the collimator angle $\theta_Z$ is an angle in a state where the height of the center of the X-ray source 10 and the center of the imaging surface 41 coincides with the height of the center $Z_C$, so the collimator angle $\theta_Z$ is corrected in accordance with deviation between the height of the center of the imaging surface 41 and the height of the center $Z_C$. In the continuous radiography, the source controller 11 operates the collimator 18 such that the collimator angles $\theta_X$ and $\theta_Z$ coincide with values calculated by the above expressions (3-1) and (3-2) or corrected values thereof.

The division exposure position setup section 119 determines each division exposure position for making an exposure of each small image capture field into which the total image capture field is divided, based on the length $Z_P$ of the total image capture field and the length FOV of the imaging surface 41 in the Z direction. To be more specific, the following expression (4) is first calculated.

$$Z_P/FOV \tag{4}$$

Figure 12:
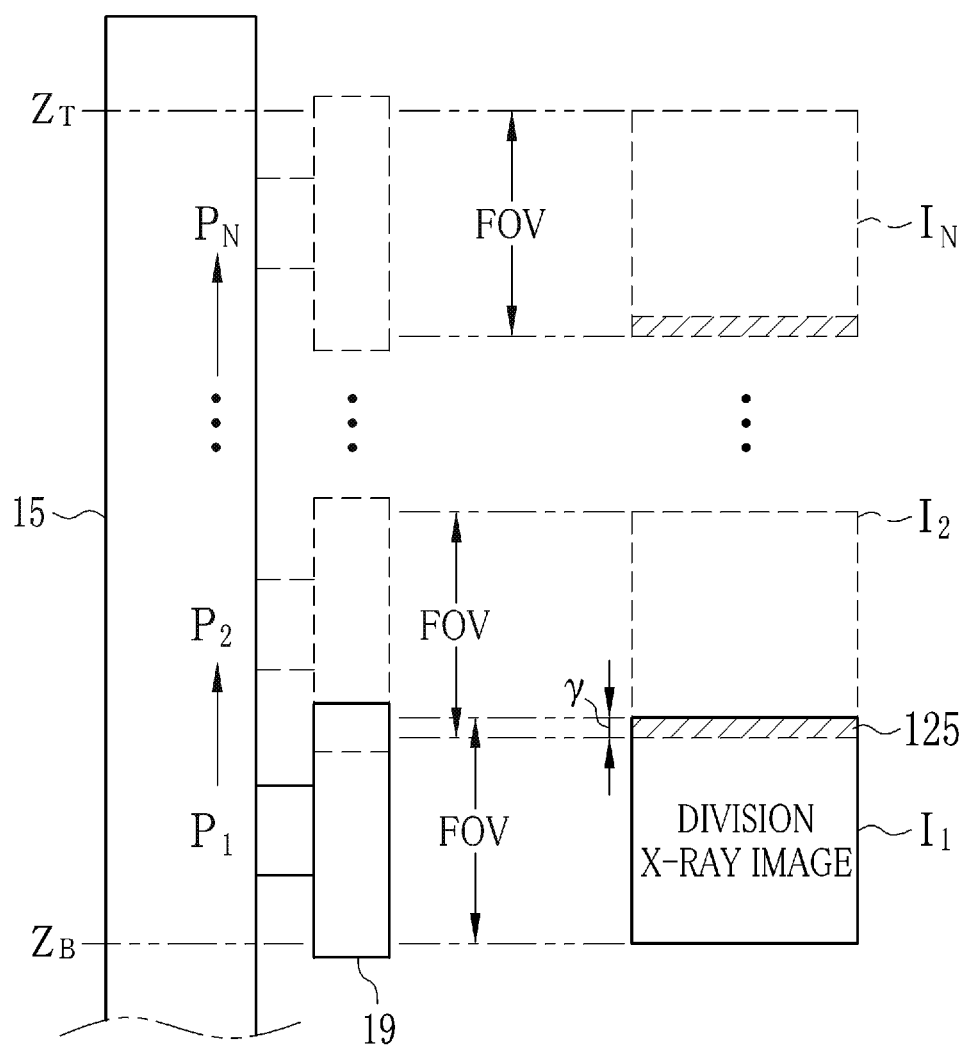
FIG. 12 is an explanatory view of division exposure positions in continuous radiography and division X-ray images obtained in the division exposure positions.

Then, to make the imaging surface 41 in one division exposure position partly overlap the imaging surface 41 in the next division exposure position, "1" is added to a result of the expression (4) if the result is an integer. If the result is not an integer, the result is rounded up. Thereby, the number N of exposures is calculated. After that, as shown in FIG. 12, in the case of the full spine radiography, the shift start position (first exposure position) $P_1$ in which a lower end of the imaging surface 41 coincides with the bottom end $Z_B$, and the shift end position (N-th exposure position) $P_N$ in which an upper end of the imaging surface 41 coincides with the top end $Z_T$ are determined. Note that, in the case of the lower limb radiography, since the electronic cassette 13 is shifted in an opposite direction, the shift start position $P_1$ is set at a position in which the upper end of the imaging surface 41 coincides with the top end $Z_T$, and the shift end position $P_N$ is set at a position in which the lower end of the imaging surface 41 coincides with the bottom end $Z_B$. The distance between the shift start position $P_1$ and the shift end position $P_N$ is equally divided by "N−1" to obtain second to (N−1)th division exposure positions $P_2$ to $P_{(N-1)}$.

Taking the case of $Z_P$=100 cm and FOV=25 cm as an example, $Z_P$/FOV is 4, being an integer. Thus, the number N of exposures is calculated at 5 from 4+1. According to the above calculations, the distance D between any two of the division exposure positions $P_1$ to $P_5$ next to each other is 18.75 cm. In the case of $Z_P$=100 cm and FOV=30 cm, $Z_P$/FOV is 3.33 . . . , not an integer. Thus, the number N of exposures is calculated at 4 by rounding up 3.33 . . . to an integer. In this case, the distance D between any two of the division exposure positions $P_1$ to $P_4$ next to each other becomes approximately 23.3 cm.

As shown in FIG. 12, the X-ray imaging system 2 makes an exposure of each small image capture field at each of the division exposure positions $P_1, P_2, \ldots,$ and $P_N$. Each division X-ray image $I_1, I_2, \ldots, I_N$ of each small image capture field has an overlap area 125, due to the overlap of the imaging surface 41 in the division exposure positions next to each other. By overlaying the overlap areas 125 of the adjacent division X-ray images, the image processor 113 produces the continuous X-ray image. The lengthy γ of this overlap area 125 is calculated by the following expression (5).

$$\gamma = \{N \times FOV - Z_P\}/(N-1) \tag{5}$$

In the above described case of $Z_P$=100 cm and FOV=25 cm, γ=(5×25−100)/2=12.5 cm. In the case of $Z_P$=100 cm and FOV=30 cm, γ=(4×30−100)/3=6.7 cm.

The division exposure position setup section 119 outputs to the operation controller 111 information on the shift start position $P_1$, the shift end position $P_N$, the calculated number N of exposures, and the distance D between the division exposure positions next to each other. Under the control of the operation controller 111, the holder shift mechanism 20 successively shifts the holder 19 by the distance D in the Z direction from the shift start position $P_1$ to the shift end position $P_N$. The source controller 11 controls the operation of the source shift mechanism 16, so the X-ray source 10 turns by the turn angle $\phi_Z$ such that the irradiation field of the X-rays coincides with the small image capture field in each division exposure position. Also, the source controller 11 controls the operation of the X-ray source 10, so that the X-rays are emitted shortly after the holder 19 is shifted to and stopped at the division exposure position and the X-ray source 10 is turned by the desired turn angle $\phi_Z$. As described above, the total image capture field is divided into the N number of small image capture fields, and the division exposure positions for making exposures of individual small image capture fields are determined.

The division exposure position setup section 119 outputs the information on the calculated length γ of the overlap area 125 to the image processor 113. Based on the information on the length γ, the image processor 113 merges the division X-ray images of the small image capture fields by overlaying the overlap areas 125, to produce the single continuous X-ray image.

The map scaling section 115 scales up or down the full spine irradiation area map 85 or the lower limb irradiation area map 86 in accordance with the size of the total image capture field determined by the total image capture field setup section 117. Since the full spine irradiation area map 85 and the lower limb irradiation area map 86 are designed based on the body size of the average adult male, as described above, the full spine irradiation area map 85 and the lower limb irradiation area map 86 sometimes do not fit the total image capture field in size, depending on the body size of the patient M. For this reason, as shown in FIG. 13, the map scaling section 115 calculates a ratio between the width $X_P$ of the total image capture field and the width $X_S$ of the full spine irradiation area map 85, or between the width $X_P$ of the total image capture field and the width $X_L$ of the lower limb irradiation area map 86. The map scaling section 115 also calculates a ratio between the length $Z_P$ of the total image capture field and the length $Z_S$ of the full spine irradiation area map 85, or between the length $Z_P$ of the total image capture field and the length $Z_L$ of the lower limb irradiation area map 86. The map scaling section 115 scales up or down the full spine irradiation area map 85 or the lower limb irradiation area map 86 in the X and Z directions using these ratios as scaling ratios. To be more specific, the coordinates of the start and end points of each irradiation area 87 to 91 are multiplied by the scaling ratios. As an example, FIG. 13 shows the case of scaling up the full spine irradiation area map 85 at a scaling ratio $X_P/X_S$ of 1.2 and a scaling ratio $Z_P/Z_S$ of 1.2. The map scaling section 115 outputs the scaled-up or -down irradiation area map to the map dividing section 116. The irradiation area maps 85 and 86 after the scaling are hereinafter called a scaled map 85' and a scaled map 86', respectively.

Figure 14:
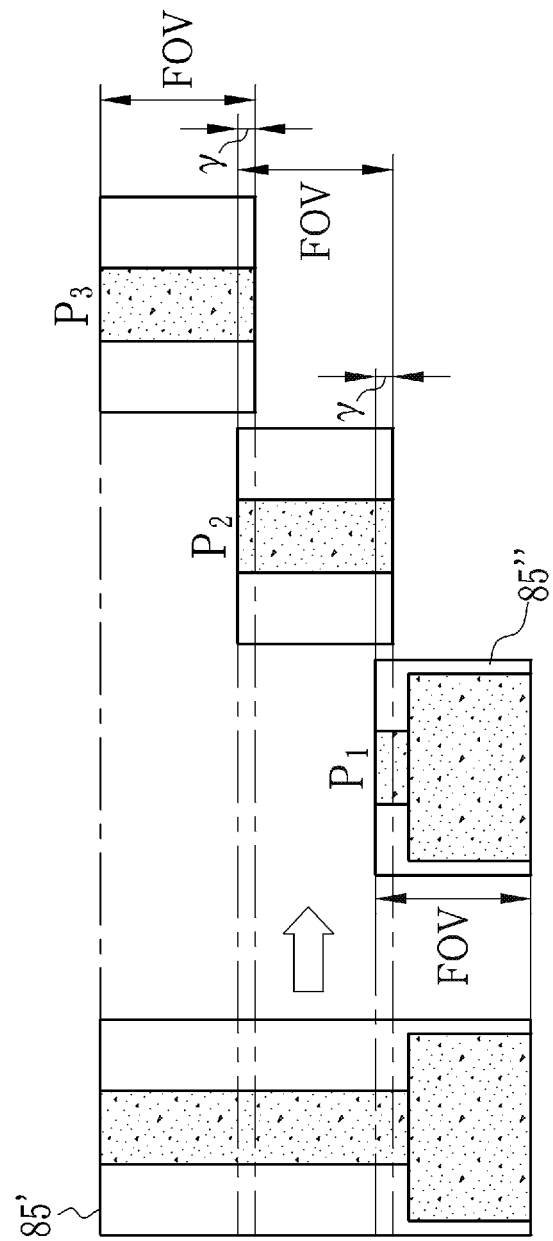
FIG. 14 is an explanatory view of the function of a map dividing section.

As shown in FIG. 14, the map dividing section 116 divides the scaled map 85' or the scaled map 86' in accordance with the size of the small image capture fields, based on the information on the distance D between the division exposure positions calculated by the division exposure position setup section 119. In FIG. 14, the number N of exposures is three, so the scaled map 85' is divided into three corresponding to the division exposure positions $P_1$ to $P_3$. The map dividing section 116 outputs to the cassette controller 112 information about the division of the scaled map 85' or the scaled map 86'. The scaled map 85' is divided into small maps 85". The scaled map 86' is divided into small maps 86".

Whenever the division exposure is performed, the cassette controller 112 provides the electronic cassette 13 with information on the small map 85" or 86" produced by the map dividing section 116 and information on the emission stop threshold value (TH1 or TH2 of FIG. 7).

The detection pixel selector 75 compares the information on the small map 85" or 86" provided by the cassette controller 112 with the information on the coordinates of the detection pixels 65, in order to select the detection pixels 65 that belong to the irradiation area. The threshold value generator 78 determines the irradiation stop threshold value used in each division exposure, based on the information on the irradiation stop threshold value provided by the cassette controller 112.

Next, a full spine continuous radiography process of the X-ray imaging system 2 will be described with referring to flowcharts of FIGS. 15 and 16.

Firstly, after the X-ray source 10 and the upright imaging support 15 are disposed in appropriate positions, the SID is measured. The SID value is inputted from the input device 105 to the console 14 at S10 of FIG. 15. Then, while the patient M stands in a predetermined position in front of the upright imaging support 15, the laser light source 21 is turned on. The height of the X-ray source 10 is adjusted by the source shift mechanism 16, and the X-ray source 10 is turned in the Z or X direction to set up the total image capture field (S11).

S10 is omitted, if an invariable SID value is inputted in advance, if the SID is fixed in accordance with the body part (the imaging condition stored in the storage device 102 includes an SID value of each body part), or if the SID is automatically calculated using a position sensor that detects the horizontal positions of the X-ray source 10 and the upright imaging support 15.

The SID value, and the height (top end $Z_T$) and the turn angles $\phi_X$ and $\phi_Z$ of the X-ray source 10 detected by the potentiometer are inputted to the operation condition setup section 110. The operation condition setup section 110 calculates the shift range of the holder 19, the collimator angle θ, the number N of exposures, the division exposure positions $P_1, P_2, \ldots$, and $P_N$, the distance D, the length γ of the overlap area 125, and the like, in its total image capture field setup section 117, collimator angle setup section 118, and division exposure position setup section 119 (S12). The above information is outputted to the operation controller 111 and the like.

The map scaling section 115 scales up or down the full spine irradiation area map 85 in accordance with the size of the total image capture field determined by the total image capture field setup section 117 to produce the scaled map 85' (S13). Then, the map dividing section 116 divides the scaled map 85' based on the distance D between the division exposure positions next to each other into size corresponding to the small image capture fields to produce the small maps 85" (S14). The information on the small maps 85" is transmitted to the electronic cassette 13 through the cassette controller 112 together with the information on the emission stop threshold value (S15).

After that, under the control of the operation controller 111, the source shift mechanism 16 and the holder shift mechanism 20 are operated. The source shift mechanism 16 moves the X-ray source 10 to the center $Z_C$ and turns the X-ray source 10 by the turn angle of the first division exposure. The holder shift mechanism 20 shifts the holder 19 to the first division exposure position $P_1$. The source controller 11 operates the collimator 18 to adjust the irradiation field in accordance with the collimator angles $θ_X$ and $θ_Z$ determined by the collimator angle setup section 118 or the corrected values thereof (S16).

After that, the X-ray imaging system 2 waits for the emission start signal (S17). When the radiological technician operates the exposure switch 12 to issue the emission start signal (YES in S17), the X-ray source 10 starts emitting the X-rays. In synchronization with this, the FPD 40 starts accumulating the signal charge, so the first division exposure is carried out (S18).

While the FPD 40 performs the charge accumulation operation, the AEC circuit 67 performs the AEC based on outputs of the detection pixels 65. As shown in FIG. 16, the detection pixel selector 75 selects one or more detection pixels 65 that belong to the irradiation area defined by the small map 85" out of all the detection pixels 65 (S30). The AEC detection signal of the selected detection pixel 65 is integrated by the integrator 76 (S31). The integration is performed whenever the sampling of the S/H 64 is performed in cycles. The integration value at each cycle is transmitted to the comparator 77.

The threshold value generator 78 produces the emission stop threshold value TH1 supplied by the cassette controller 112, and outputs the emission stop threshold value TH1 to the comparator 77. The comparator 77 compares the integration value of the detection signal from the integrator 76 with the threshold value TH1 (S32). If the integration value reaches the threshold value TH1 (YES in S33), the comparator 77 issues the emission stop signal. The emission stop signal from the comparator 77 is transmitted to the emission signal I/F 35 of the source controller 11 through the emission signal I/F 80 (S34).

When the emission signal I/F 35 receives the emission stop signal, the controller 31 of the source controller 11 stops supplying the electric power from the high voltage generator 30 to the X-ray source 10 to stop the X-ray emission. In the electronic cassette 13, the FED 40 shifts from the charge accumulation operation to the readout operation. The image data is outputted in the readout operation.

The image data outputted from the FPD 40 is transmitted to the console 14 through the communication circuit 45 by the wired or wireless method, and is subjected to the various image processes in the image processor 113. in the first division exposure, the first division X-ray image $I_1$ is obtained (S19 of FIG. 15).

In a similar manner, the holder 19 is shifted to the K-th division exposure position $P_K$ (K=2, 3, 4, . . . , N), and the X-ray source 10 is turned by the desired turn angle $\phi_Z$ with adjustment of the irradiation field (S20). The K-th division exposure is performed based on the small map 85'' corresponding to the K-th small image capture field (S21), so the K-th division X-ray image $I_K$ is obtained (S22). These steps are repeated until the number of exposures reaches N (K=N, YES in S23).

After the N-th division exposure is completed, the image processor 113 produces the continuous X-ray image from the division X-ray images $I_1$, $I_2$, . . . , and $I_N$ obtained in the division exposure positions $P_1$, $P_2$, . . . , and $P_N$ by overlaying the overlap areas 125 (S24). The display controller 114 displays the produced continuous X-ray image on the monitor 104 (S25).

As described above, the X-ray imaging system 2 has the full spine irradiation area map 85 that defines spine and pelvis areas as the irradiation areas 87 and 88, and the lower limb irradiation area map 86 that defines pelvis, knee, and ankle areas as the irradiation areas 89 to 91. Out of all the detection pixels 65 distributed in the imaging surface 41, one or more detection pixels 65 are selected based on these maps 85 and 86. Therefore, it is possible to easily determine the irradiation area in the continuous radiography, without performing preliminary exposure or providing large and complicated equipment.

Furthermore, after the irradiation area map is scaled up or down to the same size as that of the total image capture field, the scaled map is divided into the small maps in accordance with the small image capture fields. Therefore, the AEC is appropriately carried out regardless of the difference in the body size of the patient M.

The total image capture field is set up using the laser light in the above embodiment, but some X-ray imaging systems do not have the laser light source 21 and cannot set up the total image capture field. Such systems may adopt irradiation area maps of FIGS. 17A and 17B.

Figure 17A:
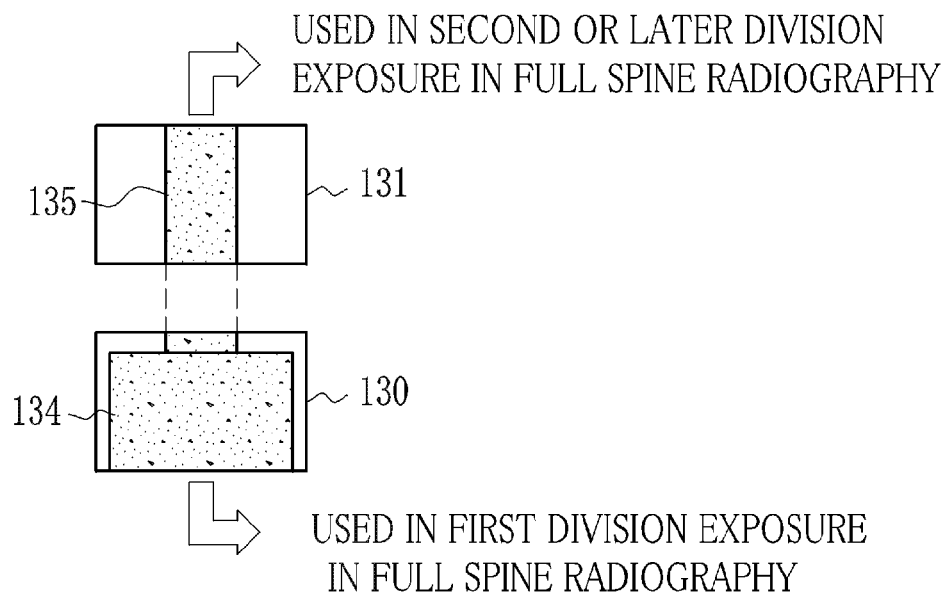
FIG. 17A is an explanatory view of first and second maps of the full spine irradiation area map.
Figure 17B:
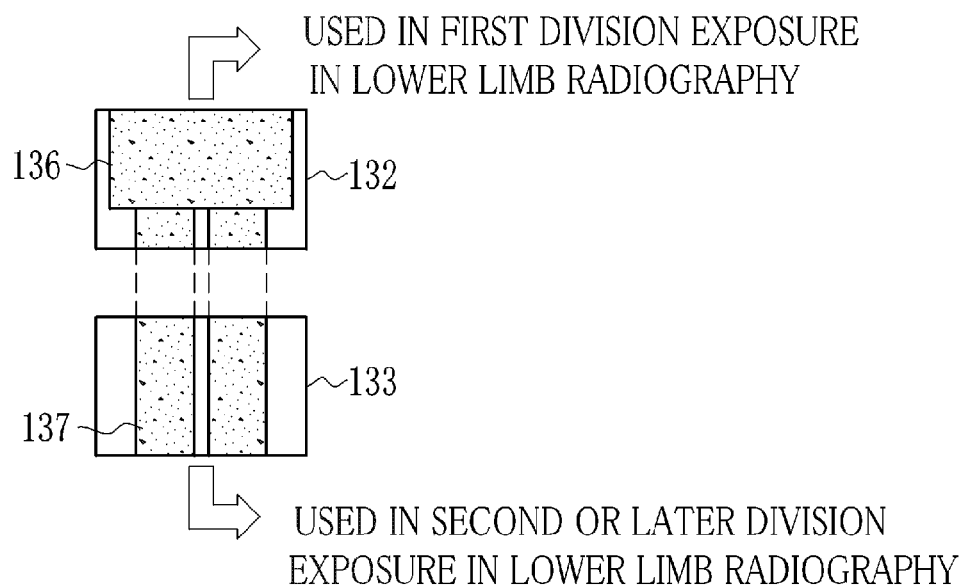
FIG. 17B is an explanatory view of first and second maps of the lower limb irradiation area map.

In FIG. 17A, a full spine irradiation area map includes a first map 130 and a second map 131. In FIG. 17B, a lower limb irradiation area map includes a first map 132 and a second map 133.

The first map 130 has an inverse T-shaped irradiation area 134 corresponding to the pelvis and a part of the spine. The first map 130 is used in the first division exposure for making an exposure of the pelvis and its vicinity in the full spine radiography. The second map 131 has a narrow and straight irradiation area 135 corresponding to the spine. The second map 131 is used in the second or later division exposure for making an exposure of the spine in the full spine radiography.

Similarly, the first irradiation map 132 has a π-shaped irradiation area 136 corresponding to the pelvis and the base of legs. The first irradiation map 132 is used in the first division exposure for making an exposure of the pelvis and its vicinity in the lower limb radiography. The second map 133 has two straight irradiation areas 137 corresponding to the legs. The second irradiation map 133 is used in the second or later division exposure for making an exposure of the legs including the knees and the ankles in the lower limb radiography.

In the case of the full spine radiography, the cassette controller 112 provides the electronic cassette 13 with the first map 130 in the first division exposure, and switches to the second map 131 in the second or later division exposure. In the case of the lower limb radiography, the first map 132 is provided in the first division exposure, and the second map 133 is provided in the second or later division exposure. To make an exposure of the pelvis and its vicinity, an irradiation area map having an irradiation area of complex shape is used, for example, the first map 130 having the inverse T-shaped irradiation area 134 and the first map 132 having the π-shaped irradiation area 136. To make an exposure of the spine or the legs, an irradiation area map having an irradiation area of simple shape is used, for example, the second map 131 having the irradiation area 135 and the second map 133 having the irradiation areas 137. Preparing two types of maps and switching the used map in accordance with the number of exposures eliminate the need for setting up the total image capture field.

In the above embodiment, in both the full spine radiography and the lower limb radiography, the pelvis is first exposed. This is because the pelvis tends to be the most important part in diagnosis. However, another body part may be first exposed instead. For example, in the case of examination of knee arthrosis in the lower limb radiography, the knee is first exposed at the first division exposure. Accordingly, in the example of FIGS. 17A and 17B, if the body part other than the pelvis is first exposed, the switching between the maps 130 and 131 or between the maps 132 and 133 is carried out in accordance with the body part, instead of the number of exposures.

In the above embodiment, the irradiation area map defines the irradiation area. The irradiation area has a margin to prevent an actual exposed area from being out of the irradiation area defined by the irradiation area map. Therefore, there is a case in which the detection pixel 65 selected by the detection pixel selector 75 is in a non-exposed area (area to which the X-rays are not applied) or a directly-exposed area (area to which the X-rays are directly applied without passing through the body of the patient M). In such a case, the AEC is carried out improperly. Thus, the detection pixel selector is preferably constituted as follows.

As shown in FIG. 18, a detection pixel selector 140 is provided with an exposed area determination section 141, a body area determination section 142, and a predicted dose calculator 143. The exposed area determination section 141 determines the actual exposed area in the imaging surface 41 from the collimator angles $\theta_Z$ and $\theta_Z$, the SID, the division exposure position, and the turn angle $\phi_Z$ of the X-ray source 10. The exposed area determination section 141 picks up the AEC detection signals of the detection pixels 65 present within the actual exposed area, out of the AEC detection signals of the detection pixels 65 present within the irradiation area defined by the irradiation area map. In other words, the AEC detection signals of the detection pixels 65 that are present in the irradiation area overlapping with the non-exposed area are excluded (S40 of FIG. 19).

The body area determination section 142 picks up the AEC detection signals of the detection pixels 65 present within a body area, out of the AEC detection signals of the detection pixels 65 present within the actual exposed area of the irradiation area defined by the irradiation area map. Thus, the AEC detection signals of the detection pixels 65 present in the directly-exposed area are excluded.

The predicted dose calculator 143 calculates an X-ray dose (predicted dose) that should be incident on the directly-exposed area in this situation from a relational expression with parameters such as the SID, the division exposure position, the turn angle $\phi_Z$ of the X-ray source 10, and the imaging condition including the tube voltage and the tube current (S41 of FIG. 19). The predicted dose calculator 143 outputs an instantaneous value of the predicted dose to the body area determination section 142. Note that, the operation condition setup section 110 calculates the various parameters required for the determination of the actual exposed area and the calculation of the predicted dose. The calculated parameters are obtained through the cassette controller 112.

The body area determination section 142 compares the AEC detection signal of each detection pixel 65 present within the actual exposed area of the defined irradiation area with the instantaneous value of the predicted dose obtained by the predicted dose calculator 143 (S42 of FIG. 19). If the AEC detection signal is equal to or larger than the instantaneous value of the predicted dose, the detection pixel 65 is judged to be present in the directly-exposed area. If not, the detection pixel 65 is judged to be present in the body area (S43 of FIG. 19). In another case, if the AEC detection signal is within a predetermined range around the instantaneous value of the predicted dose (range of the instantaneous value±α), the detection pixel 65 may be judged to be present in the directly-exposed area. In this manner, out of the AEC detection signals of the detection pixels 65 belonging to the defined irradiation area, the AEC detection signals of the detection pixels 65 present in the non-exposed area or the directly-exposed area are excluded. The determination of the actual exposed area and the body area (exclusion of the non-exposed area and the directly-exposed area) is carried out concurrently with the transmission of the AEC detection signals during the radiography. The exclusion of the AEC detection signals from the detection pixels 65 in the non-exposed area or the directly-exposed area facilitates improved accuracy of the AEC.

Note that, FIG. 18 shows a state in which the exposed area determination section 141 excludes the detection pixels 65 present within portions 144 of the irradiation area 88 overlapping with the non-exposed areas, and furthermore, the body area determination section 142 excludes the detection pixels 65 present within portions 145 of the irradiation area 88 overlapping with the directly-exposed areas.

The setup of the total image capture field may be performed in another way than described above. For example, a visible light source for applying rectangular visible light through the collimator 18 to the patient N may be provided instead of the laser light source 21 described above. In this case, the collimator angles $\theta_X$ and $\theta_Y$ are adjusted such that the desired total image capture field is irradiated with the rectangular visible light, and the size of the total image capture field is geometrically calculated based on the adjusted collimator angles $\theta_X$ and $\theta_Y$ and the SID. In another case, an aiming device such as the laser light source 21 may be provided not in the X-ray source 10 but in the holder 19. In further another case, without providing the aiming device, the size of the total image capture field may be measured by a ruler, and a measurement value may be inputted from the input device 105.

If the ratio of the length y of the overlap area 125 relative to the length FOV of the imaging surface 41 in the Z direction is too large, the patient N is exposed to much doses at the overlap areas 125, so it is preferable to set an upper limit on the length γ (for example, 10% of the FOV). The length γ calculated from the above expression (5) is compared with the predetermined upper limit. If the length γ is larger than the upper limit, the division exposure positions $P_1, P_2, \ldots,$ and $P_N$ are equally shifted in the Z direction so that the length γ is within the upper limit.

In another case, the length γ may be always set constant. In this case, the imaging surface 41 may be out of the total image capture field in the N-th division exposure. The X-rays are applied only to an upper or lower part of the imaging surface 41 in the N-th division exposure.

The irradiation area map may include a weighting coefficient by which the AEC detection signals of the detection pixels 65 belonging to the irradiation area are multiplied. The weighting coefficient is set lower at a portion important for diagnosis in the irradiation area, for example, at a portion of bones of the knees in the irradiation area 90. In outputting the AEC detection signals to the AEC circuit 67, the AEC detection signals are multiplied by the weighting coefficient, so the portion having the lower weighting coefficient is exposed to more X-rays than the other portions. This allows obtainment of the X-ray image that is sharp at the portion important for diagnosis.

In the above embodiment, since the normal pixels 50 and the detection pixels 65 are present independently, the defect correction has to be carried out in which the pixel values of the row having the detection pixel 65 are interpolated using the pixel values of the adjacent row without having the detection pixel 65. The defect correction, however, possibly decreases image quality of the X-ray image. Accordingly, use of an FPD 150 of FIG. 20 eliminates the need for the defect correction.

In FIG. 20, the FPD 150 is provided with a normal pixel 151 for producing the X-ray image and a detection pixel 152 that doubles the functions of production of the X-ray image and the AEC. The normal pixels 151 and the detection pixels 152 are arranged in a matrix, and the ratio between the number of the normal pixels 151 and that of the detection pixels 152 is appropriate, as with the normal pixels 50 and the detection pixels 65 of the above embodiment. The normal pixel 151 has two photodiodes 153 and 154, and the detection pixel 152 has two photodiodes 155 and 156. The photodiodes 153 and 154 of the normal pixel 151 are connected in parallel, and one end of the photodiodes 153 and 154 is connected to the signal line 57 through the TFT 52. On the other hand, as for the detection pixel 152, the photodiode 155 is connected to the signal line 57 through the TFT 52 at its one end, as with the photodiode 153 of the normal pixel 151, while the photodiode 156 is connected to the signal line 57 directly without through the TFT.

The normal pixel 151 discharges the electric charge accumulated in the two photodiodes 153 and 154. The detection pixel 152, on the other hand, discharges the electric charge accumulated only in the photodiode 155. The accumulated charge amount of the detection pixel 152 is approximately half of that of the normal pixel 151, because the photodiode 156 for use in the AEC does not contribute to the production of the X-ray image. Even though, the FPD 150 can prevent deterioration in the image quality as compared with a case where the detection pixel 65 outputs no pixel value and the defect correction is performed to compensate for the pixel value. A multiplying coefficient by which the pixel value of the detection pixel 152 is to be multiplied is calculated in advance based on the incident area size of the photodiodes 153 to 156. If the output of the detection pixels 152 is corrected by multiplication, the X-ray image can be produced without performing the defect correction. Thus, it is possible to almost completely eliminate adverse effect on the image quality of the X-ray image due to the provision of the detection pixels for the AEC.

The above embodiment is described with taking the case of standing-position radiography in which the holder 19 is shifted in the vertical direction along the standing patient M as an example, but the present invention is also applicable to lying-position radiography in which the holder is shifted in a horizontal direction along the patient lying on an imaging table. The holder 19 is shifted along the body axis of the patient M in the above embodiment, but may be shifted in a direction other than that of the body axis in the continuous radiography.

The X-ray source 10 is turnable in the above embodiment, but a linearly shiftable X-ray source may be used instead. Furthermore, the holder 19 and the X-ray source 10 may keep moving during the radiography, instead of intermittently stopping at each division exposure position.

If a defect occurs in the detection pixel 65 of the electronic cassette 13, or the communication between the source controller 11 and the electronic cassette 13 is stopped during the radiography due to electrical shorting, the emission stop signal may not be transmitted appropriately and the AEC possibly malfunctions. Since the source controller 11 sets up the maximum product value (mAs value) in the imaging condition, the malfunction of the AEC may cause excessive dose to the patient. Thus, the electronic cassette 13 is put in a test mode immediately after installation or at the beginning of a day to carry out test radiography on every exposure condition prepared on the console 14. Furthermore, the detection pixels 65 keep detecting the X-rays even after the electronic cassette 13 transmits the emission stop signal to the source controller 11. If the stop of the X-ray emission is detected within a predetermined time period, it is judged that the AEC works normally. If the stop of the X-ray emission is not detected, it is judged that some failure has occurred, so a warning message is displayed on the monitor 104.

In a case where the emission single I/F 35 of the source controller 11 is connectable to the emission signal I/F 80 of the electronic cassette 13 in both the wired and wireless methods, if wireless communication is judged to he unstable as a result of monitoring radio field intensity, a warning may be displayed to recommend switching to the wired method.

In the above embodiment, the detection pixel 65 that is connected to the signal line 57 directly without through the TFT 52 is used as the AEC sensor (dose detection sensor). Instead of this, with taking advantage of the fact that electric current flows through the bias line 53, which supplies the bias voltage Vb to each pixel, by a current value proportional to the amount of the electric charge produced in the pixel, the dose may be detected by monitoring the electric current flowing through the bias line 53 connected to the specific normal pixel 50. In further another case, the dose may be detected based on leak charge from the normal pixel 50 in a state where all the TFTs 52 are turned off. Furthermore, another AEC detection pixel that is operated independently of the normal pixels 40 may be provided in the imaging surface 41.

The console 14 and the electronic cassette 13 are separate in the above embodiment, but the console 14 may not be necessarily independent of the electronic cassette 13. The electronic cassette 13 may have the function of the console 14. Likewise, the source controller 11 and the console 14 maybe integrated into one unit. The present invention may be applied to a support-mounted type X-ray image detecting device, instead of the electronic cassette being the portable X-ray image detecting device. The X-ray imaging system according to the present invention can carryout normal radiography for making an exposure of a single frame, in addition to the continuous radiography.

The present invention is applicable to a radiation imaging system using another type of radiation such as γ-rays instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging system for dividing a total image capture field into N integer number of small image capture fields, and producing a single continuous radiographic image from N number of division radiographic images obtained by division exposures of said small image capture fields, said radiation imaging system comprising:
   a radiation source for emitting radiation to each of said small image capture fields;
   a radiation image detecting device having a detection panel having an imaging surface having an arrangement of a plurality of pixels, said detection panel detecting said radiation that has passed through a body part of said small image capture field to produce said division radiographic image;
   a plurality of dose detection sensors substantially uniformly distributed in said imaging surface, each for measuring a radiation dose;
   a memory for storing an irradiation area map that defines as an irradiation area an area for measuring said radiation dose in accordance with said body part to be imaged;
   a map scaling section for scaling up or down said irradiation area map so as to make said irradiation area map coincide with said total image capture field in size;
   a dose detection sensor selector for selecting one or more of said dose detection sensors belonging to said irradiation area based on said irradiation area map that has been scaled up or down by said map scaling section; and
   an automatic exposure controller for automatically controlling a radiation exposure in each of said division exposures, said automatic exposure controller stopping emission of said radiation from said radiation source in accordance with a measurement value obtained from a detection signal of said dose detection sensor selected by said dose detection sensor selector.

2. The radiation imaging system according to claim 1, further comprising a map dividing section for dividing said irradiation area map that has been scaled up or down by said map scaling section in accordance with said small image capture fields.

3. The radiation imaging system according to claim 1, wherein said measurement value is an integration value of said detection signal of said selected dose detection sensor; and wherein the automatic exposure controller is arranged so that when said integration value reaches a predetermined threshold value, the emission of said radiation is stopped.

4. The radiation imaging system according to claim 3, wherein said irradiation area map includes:
a full spine irradiation area map for defining said irradiation areas corresponding to a pelvis and a spine; and
a lower limb irradiation area map for defining said irradiation areas corresponding to said pelvis, knees, and ankles.

5. The radiation imaging system according to claim 3, wherein
said irradiation area map includes a first map for defining said irradiation area of a first shape and a second map for defining said irradiation area of a second shape; and
said dose detection sensor selector being arranged to switch between said first map and said second map in accordance with a number of said division exposures or said small image capture field.

6. The radiation imaging system according to claim 5, wherein
said first map defines said irradiation area of inverse T shape corresponding to a pelvis and a part of a spine; and
said second map defines said irradiation area being narrow and straight corresponding to said spine.

7. The radiation imaging system according to claim 5, wherein
said first map defines said irradiation area of $\pi$ shape corresponding to a pelvis and a part of legs; and
said second map defines two of said irradiation areas being straight corresponding to said legs.

8. The radiation imaging system according to claim 4, wherein when said small image capture field to be first exposed includes said pelvis, said dose detection sensor selector is arranged to use said first map in a first exposure, and to use said second map in a second or later exposure.

9. The radiation imaging system according to claim 3, wherein
said dose detection sensor selector includes an exposed area determination section for determining an actual exposed area based on an angle of a collimator of said radiation source and a positional relation between said radiation source and said radiation image detecting device; and
said dose detection sensor selector is arranged to select one or more of said dose detection sensors that are present within said actual exposed area determined by said exposed area determination section and belong to said irradiation area.

10. The radiation imaging system according to claim 3, wherein said N number of small image capture fields partly overlap one another.

11. The radiation imaging system according to claim 3, wherein said plurality of pixels include:
a normal pixel for producing signal charge by an amount corresponding to said radiation dose, and accumulating said signal charge, and outputting said signal charge to a signal line through a switching element; and
a detection pixel directly connected to said signal line, for functioning as said dose detection sensor.

12. The radiation imaging system according to claim 1, wherein said radiation image detecting device is an electronic cassette having said detection panel contained in a portable housing.

13. A radiation imaging system for dividing a total image capture field into N integer number of small image capture fields, and producing a single continuous radiographic image from N number of division radiographic images obtained by division exposures of said small image capture fields, said radiation imaging system comprising:
a radiation source for emitting radiation to each of said small image capture fields;
a radiation image detecting device having a detection panel having an imaging surface having an arrangement of a plurality of pixels, said detection panel detecting said radiation that has passed through a body part of said small image capture field to produce said division radiographic image;
a plurality of dose detection sensors substantially uniformly distributed in said imaging surface, each for measuring a radiation dose;
a memory for storing an irradiation area map that defines as an irradiation area an area for measuring said radiation dose in accordance with said body part to be imaged;
a dose detection sensor selector for selecting one or more of said dose detection sensors belonging to said irradiation area based on said irradiation area map; and
an automatic exposure controller for automatically controlling a radiation exposure in each of said division exposures, said automatic exposure controller stopping emission of said radiation from said radiation source in accordance with a measurement value obtained from a detection signal of said dose detection sensor selected by said dose detection sensor selector,
wherein said measurement value is an integration value of said detection signal of said selected dose detection sensor; and wherein the automatic exposure controller is arranged so that when said integration value reaches a predetermined threshold value, the emission of said radiation is stopped, and
wherein said dose detection sensor selector further includes:
a predicted dose calculator for calculating an instantaneous value of a predicted dose received by a directly-exposed area of said imaging surface based on an operation condition of said radiation source and a positional relation between said radiation source and said radiation image detecting device, said radiation being directly incident upon said directly-exposed area without passing through said body part; and
a body area determination section for determining a body area from a result of comparison between an instantaneous value of said detection signal of said dose detection sensor and said instantaneous value of said predicted dose,
wherein said dose detection sensor selector is arranged to select one or more of said dose detection sensors that are present within said body area and belong to said irradiation area.

14. A method for taking a continuous radiographic image comprising the steps of:
determining a total image capture field;
dividing said total image capture field into a plurality of small image capture fields in accordance with a size of a detection panel of a radiation image detecting device;
intermittently carrying out a plurality of division exposures, while relatively shifting a radiation source and said radiation image detecting device in accordance with each of said small image capture fields;

in each of said division exposures, reading out an irradiation area map corresponding to said small image capture field, said irradiation area map defining an irradiation area;

scaling up or down said irradiation area map so as to make said irradiation area map coincide with said total image capture field in size;

after the scaling step, selecting one or more dose detection sensors for use in automatic exposure control based on said irradiation area map that has been scaled up or down in said scaling step, said dose detection sensors being substantially uniformly distributed in an imaging surface of said detection panel;

stopping emission of radiation from said radiation source in accordance with a measurement value obtained by a detection signal of said selected dose detection sensor;

producing a single continuous radiographic image from a plurality of division radiographic images obtained by said division exposures.

15. The method according to claim 14, wherein said measurement value is an integration value of said detection signal of said selected dose detection sensor; and when said integration value reaches a predetermined threshold value, the emission of said radiation is stopped.

* * * * *